United States Patent
Kiwan et al.

(10) Patent No.: US 10,801,462 B2
(45) Date of Patent: Oct. 13, 2020

(54) FUEL COMPOSITION AND AGING ESTIMATION

(71) Applicant: Ford Global Technologies, LLC, Dearborn, MI (US)

(72) Inventors: Rani Kiwan, Ann Arbor, MI (US); Gopichandra Surnilla, West Bloomfield, MI (US); Christopher Paul Glugla, Macomb, MI (US); Mark Meinhart, Dexter, MI (US); Ross Dykstra Pursifull, Dearborn, MI (US); Mohannad Hakeem, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 52 days.

(21) Appl. No.: 16/281,012

(22) Filed: Feb. 20, 2019

(65) Prior Publication Data
US 2020/0263653 A1 Aug. 20, 2020

(51) Int. Cl.
*F02D 41/38* (2006.01)
*G01N 33/28* (2006.01)
(Continued)

(52) U.S. Cl.
CPC .......... *F02P 5/045* (2013.01); *F02D 19/0634* (2013.01); *F02D 19/084* (2013.01);
(Continued)

(58) Field of Classification Search
CPC ............ F02D 41/0025; F02D 41/3005; F02D 41/3809; F02D 41/401; F02D 19/0634;
(Continued)

(56) References Cited

U.S. PATENT DOCUMENTS

| 7,516,652 B2 | 4/2009 | Schulz et al. |
| 7,523,723 B2 | 4/2009 | Marriott et al. |

(Continued)

FOREIGN PATENT DOCUMENTS

| CN | 101231225 A | 7/2008 |
| CN | 105527011 A | 4/2016 |

(Continued)

OTHER PUBLICATIONS

Kiwan, R. et al., "Fuel Composition and Aging Estimation," U.S. Appl. No. 16/280,995, filed Feb. 20, 2019, 90 pages.

(Continued)

*Primary Examiner* — Sizo B Vilakazi
*Assistant Examiner* — Anthony L Bacon
(74) *Attorney, Agent, or Firm* — Geoffrey Brumbaugh; McCoy Russell LLP

(57) ABSTRACT

Methods and systems are provided for estimating ethanol content in fuel, water content in fuel, and an age of the fuel in a vehicle engine. In one example, a method may include estimating fuel ethanol content, water content, or fuel age based on a resonant frequency (f) of pressure pulsations, a change in fuel rail pressure ($\delta p$), and a damping coefficient ($\alpha$) of pressure pulsations in the fuel rail as estimated after a fuel injection or a pump stroke. One or more engine operating parameters may be adjusted based on the estimated fuel ethanol content, water content, and fuel age.

20 Claims, 19 Drawing Sheets

(51) Int. Cl.
   *G01N 29/036*   (2006.01)
   *F02D 19/08*    (2006.01)
   *F02D 19/06*    (2006.01)
   *F02P 5/04*     (2006.01)
   *G07C 5/08*     (2006.01)
   *F02P 5/15*     (2006.01)

(52) U.S. Cl.
   CPC ............ *F02D 41/3809* (2013.01); *F02P 5/15* (2013.01); *G01N 29/036* (2013.01); *G01N 33/2829* (2013.01); *G01N 33/2835* (2013.01); *G07C 5/0816* (2013.01); *F02D 2200/0602* (2013.01); *F02D 2200/0606* (2013.01); *F02D 2200/0612* (2013.01)

(58) Field of Classification Search
   CPC ............ F02D 19/0636; F02D 19/0655; F02D 19/084; F02D 19/085; F02D 19/087; F02D 19/088; G01N 29/036; G01N 33/2829; G01N 33/2835; G01N 33/2852
   See application file for complete search history.

(56) References Cited

U.S. PATENT DOCUMENTS

| | | | |
|---|---|---|---|
| 7,966,686 B2 | 6/2011 | Turner | |
| 7,987,704 B2 | 8/2011 | Lucido et al. | |
| 8,042,384 B2 | 10/2011 | Bailey | |
| 8,090,520 B2 | 1/2012 | Tate, Jr. et al. | |
| 8,290,684 B2 | 10/2012 | Yuen et al. | |
| 8,365,585 B2 | 2/2013 | Barra et al. | |
| 8,694,186 B2 | 4/2014 | Syed et al. | |
| 8,768,599 B2 | 7/2014 | Blanchard et al. | |
| 8,787,727 B2 | 7/2014 | Park et al. | |
| 9,157,389 B2 | 10/2015 | Nonoyama et al. | |
| 9,243,598 B2 | 1/2016 | Pursifull et al. | |
| 9,310,237 B2 | 4/2016 | Ramsay | |
| 9,403,427 B2 | 8/2016 | Haladyna et al. | |
| 9,528,448 B2 | 12/2016 | Makled et al. | |
| 9,623,858 B2 | 4/2017 | Sangameswaran et al. | |
| 9,657,680 B2 | 5/2017 | Sumilla et al. | |
| 9,688,270 B2 | 6/2017 | Amin | |
| 2008/0167788 A1 | 7/2008 | Tate et al. | |
| 2009/0178474 A1 | 7/2009 | Bailey | |
| 2009/0217753 A1* | 9/2009 | Burns | G01N 29/032 73/290 V |
| 2011/0208409 A1 | 8/2011 | Snyder et al. | |
| 2013/0030616 A1* | 1/2013 | Syed | F02D 41/30 701/22 |
| 2014/0096591 A1* | 4/2014 | Caldwell | G01F 23/2962 73/24.01 |
| 2015/0240771 A1 | 8/2015 | Pursifull et al. | |
| 2016/0010569 A1* | 1/2016 | Dunn | F02D 19/0642 123/304 |
| 2016/0320363 A1 | 11/2016 | Kylstrom et al. | |
| 2016/0363084 A1* | 12/2016 | Hoshi | F02D 41/0025 |
| 2017/0002681 A1* | 1/2017 | Desai | F02C 9/28 |

FOREIGN PATENT DOCUMENTS

| | | |
|---|---|---|
| DE | 102008013776 A1 | 10/2008 |
| DE | 102010034133 A1 | 2/2012 |
| EP | 0651150 A2 | 5/1995 |
| EP | 0860601 A2 | 8/1998 |
| GB | 2516656 A | 2/2015 |
| WO | 2013114324 A1 | 8/2013 |
| WO | 2016188647 A1 | 12/2016 |

OTHER PUBLICATIONS

Kashid, R. et al., "Fuel Composition and Aging Estimation," U.S. Appl. No. 16/281,029, filed Feb. 20, 2019, 89 pages.

* cited by examiner

FUEL COMPOSITION AND AGING ESTIMATION

FIELD

The present description relates generally to methods and systems for estimating ethanol content in fuel and an age of the fuel in a vehicle engine.

BACKGROUND/SUMMARY

Flexible fuel vehicles (FFVs) are an alternative to conventional gasoline-driven vehicles and include an internal combustion engine to combust mixtures of gasoline and a secondary fuel, such as ethanol, methanol, propanol, or other alcohols and octane improvers. Fuel blends incorporating ethanol are particularly popular due to a derivation of ethanol from biomass, with various feedstocks available from agriculture. A flexible fuel engine may be adapted to burn fuel mixtures of 0-100% ethanol, thereby reducing the well-to-wheel carbon footprint compared to gasoline. In hybrid vehicles, fuel may remain unused in the fuel tank as the vehicle may be propelled for prolonged periods solely using motor torque. Aging may cause changes in fuel composition. For example, to determine suitable air-fuel ratios at combustion chambers of the engine, the PCM may utilize an estimate or measurement of the fuel composition (e.g., percentage of ethanol) and an age of fuel to determine an amount of fuel to be injected.

Various approaches are provided for estimating ethanol content in a flexible fuel. For example, in U.S. Pat. No. 7,523,723, Marriott et al. discloses a method for determining ethanol content in fuel based on fuel rail pressure characteristics. An effective bulk modulus of the fuel and a pressure perturbation signature may be determined from the fuel rail pressure and fuel ethanol content may be estimated based on one or more of the effective bulk modulus of the fuel and the pressure perturbation signature.

However, the inventors herein have recognized potential disadvantages with the above approach. As one example, Marriott et al. does not disclose a method for determining water content absorbed by ethanol or an age of fuel in the fuel tank. Due to absorption of water by ethanol in fuel that has been idle for a prolonged duration, a phase separation may occur, rendering the fuel ineffective for engine operation. In gasoline fuels, lighter and more volatile ends (molecules with fewer Carbon atoms e.g. $C_3$ and $C_4$) may evaporate leaving behind an aged gasoline fuel with higher concentration of heavier less volatile ends. In hybrid vehicles, fuel aging may be significant as the engine may not be operated for prolonged durations. The concentration of the lighter and the heavier ends may affect a desired amount of fuel injected for combustion. A dedicated sensor may be used for fuel composition or age determination, however adding a separate component may increase manufacturing costs.

The inventors herein have recognized that the issues described above may be addressed by a method for an engine comprising: adjusting engine operation based on an estimated fuel age, the fuel age estimated based on at least two of a resonant frequency of pressure pulsations, a change in fuel rail pressure, and a damping coefficient of pressure pulsations in a fuel rail after a fuel injection. Engine operations may be further adjusted based on an estimated ethanol and water contents in the fuel, the ethanol and water contents estimated based on the resonant frequency of pressure pulsations, the change in fuel rail pressure, and the damping coefficient of pressure pulsations in a fuel rail after a fuel injection. In this way, by monitoring fuel characteristics as estimated by existing sensors fuel ethanol content, fuel water content, and fuel aging may be estimated.

In one example, a fuel ethanol content measurement may be carried out immediately after a refueling event and a fuel aging and water content estimation may be carried out periodically. In another example, a fuel aging estimation may be carried out periodically. During operation of a fuel pump, fuel rail pressure may be estimated via a fuel rail pressure sensor. A pulsation frequency, a change in pressure, and a damping coefficient of pressure pulsations maybe estimated after a fuel injection or a pump stroke. In absence of a fuel rail temperature sensor, in a flex fuel vehicle, fuel ethanol content may be estimated as a function of the pulsation frequency, the change in pressure, and the damping coefficient of pressure pulsations. Also, water content in fuel may be estimated as a different function of the pulsation frequency, the change in pressure, and the damping coefficient of pressure pulsation. In gasoline engines, fuel aging which is a function of gasoline lighter and heavier ends concentrations may also be estimated as a function of two or more of the pulsation frequency, the change in pressure, and the damping coefficient of pressure pulsations. Based on the estimated fuel ethanol content, fuel water content, and fuel age, engine operating parameters including spark timing and fuel injection amount may be adjusted. If the fuel water content is higher than a threshold, the operator may be notified to use/change the fuel in the fuel tank.

In this way, by using fuel properties as estimated by existing fuel system sensors fuel ethanol content, water content, fuel age, and/or fuel rail temperature may be determined. By eliminating the need for dedicated fuel composition detection sensor and fuel rail temperature sensor, components cost may be reduced. In a flex fuel vehicle, by determining fuel ethanol content after each refueling event, a resultant ethanol content in the fuel caused by mixing of fuel previously present in the tank and the newly delivered fuel may be estimated and used for determining air-fuel ratio. The technical effect of periodically estimating fuel aging in gasoline is that degraded fuel may be timely identified and reported to the operator to maintain engine functionality. By adjusting engine operating parameters based on fuel ethanol content, fuel water content, or fuel age, engine performance, fuel efficiency, and emissions quality may be improved.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 11:
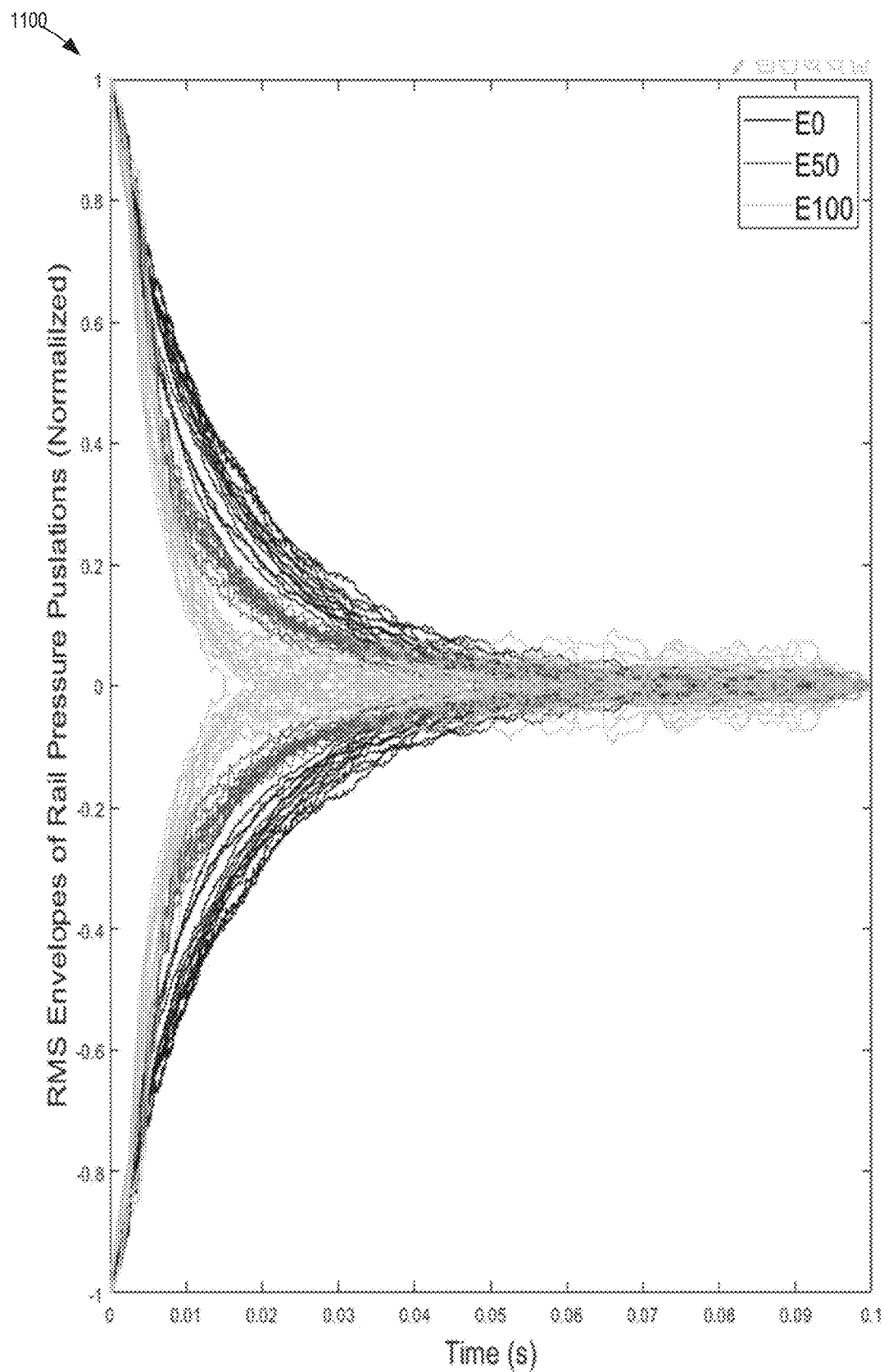
FIG. 11 shows a relationship between ethanol content in fuel and the damping of fuel rail pressure pulsations.
Figure 12:
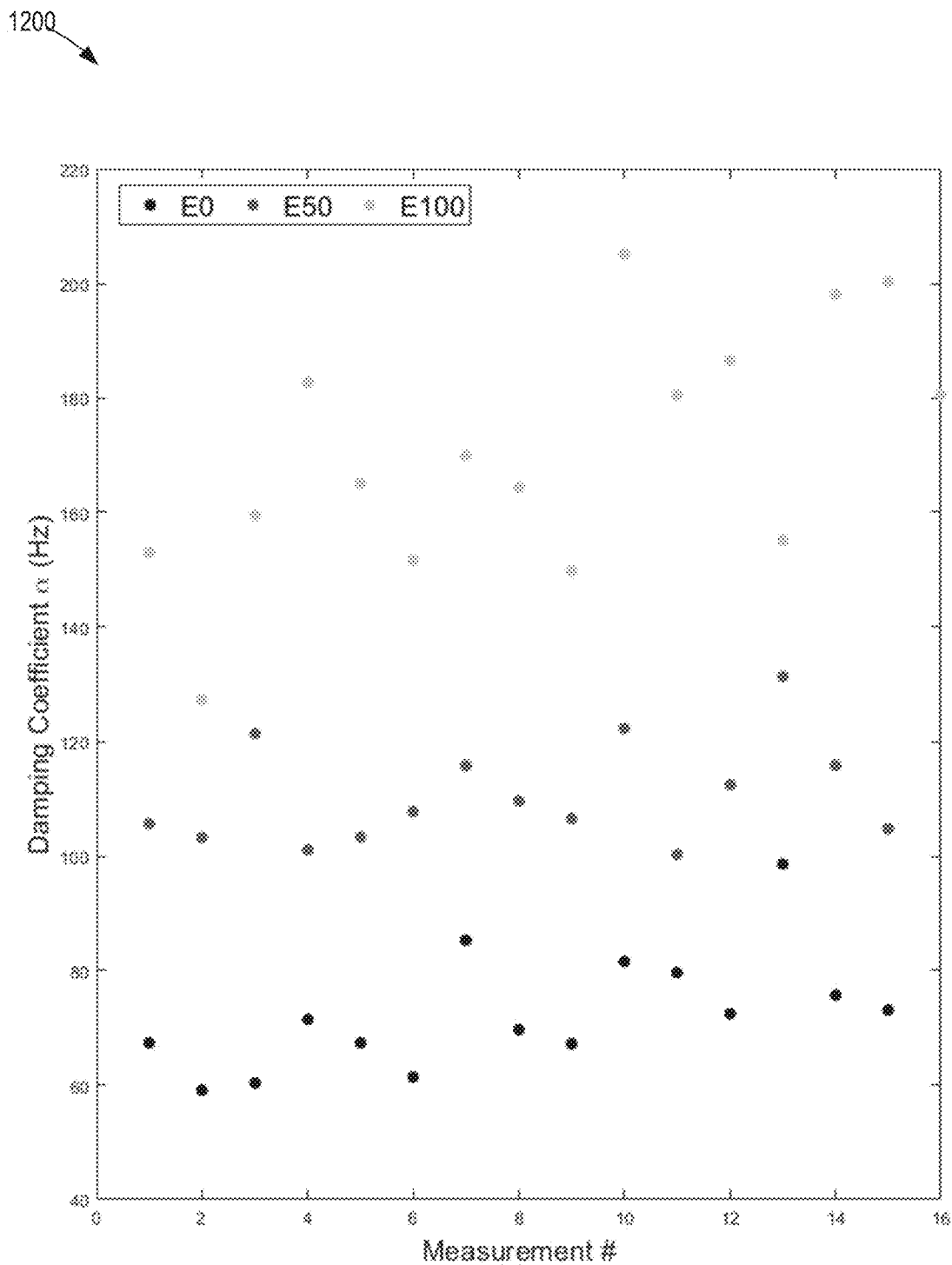
FIG. 12 shows a relationship between ethanol content in fuel and damping coefficient.
Figure 13:
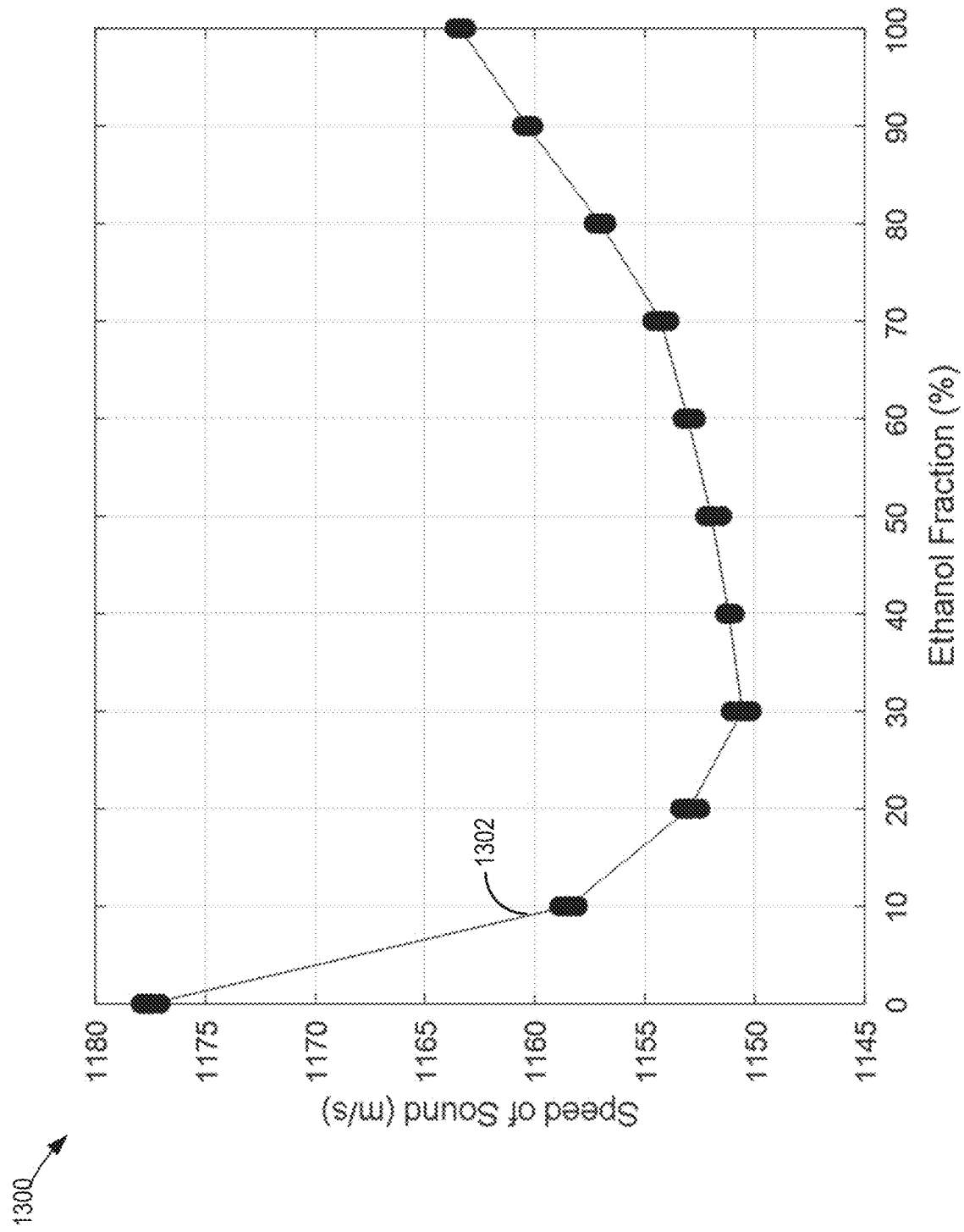
FIG. 13 shows a relation between ethanol content in fuel and the speed of sound through fuel.

The following description relates to systems and methods for estimating ethanol content, water content, and an age of fuel contained in an engine fuel tank. An example embodiment of a cylinder in an internal combustion engine with each of a direct fuel injector and a port fuel injector is given in FIG. 1. FIG. 2 depicts a fuel system that may be used with the engine of FIG. 1. An engine controller may be configured to perform example routines, such as according to the methods described in FIGS. 3-6 for determining ethanol and water content in fuel and fuel aging based on fuel rail temperature, change in fuel rail pressure, fuel rail pressure pulsation frequency, and a damping co-efficient of pressure pulsations following fuel injection or a fuel pump stroke. The engine controller may also be configured to determine fuel ethanol content and fuel age based on attenuation of ultrasonic signal in fuel, as described in FIGS. 17-18. Example plots 7-10 show variation in pressure due to fuel pump stroke, fuel injection, resonance frequency vibrations, and damping of pressure vibrations, respectively. An example relationship between fuel ethanol content and fuel rail pressure pulsations, damping coefficient of pressure pulsations, and speed of sound in fuel, respectively are shown in FIGS. 11-13. Example determinations of the fuel ethanol content and fuel age are shown in FIGS. 14, 15, 18 and 19.

Figure 1:
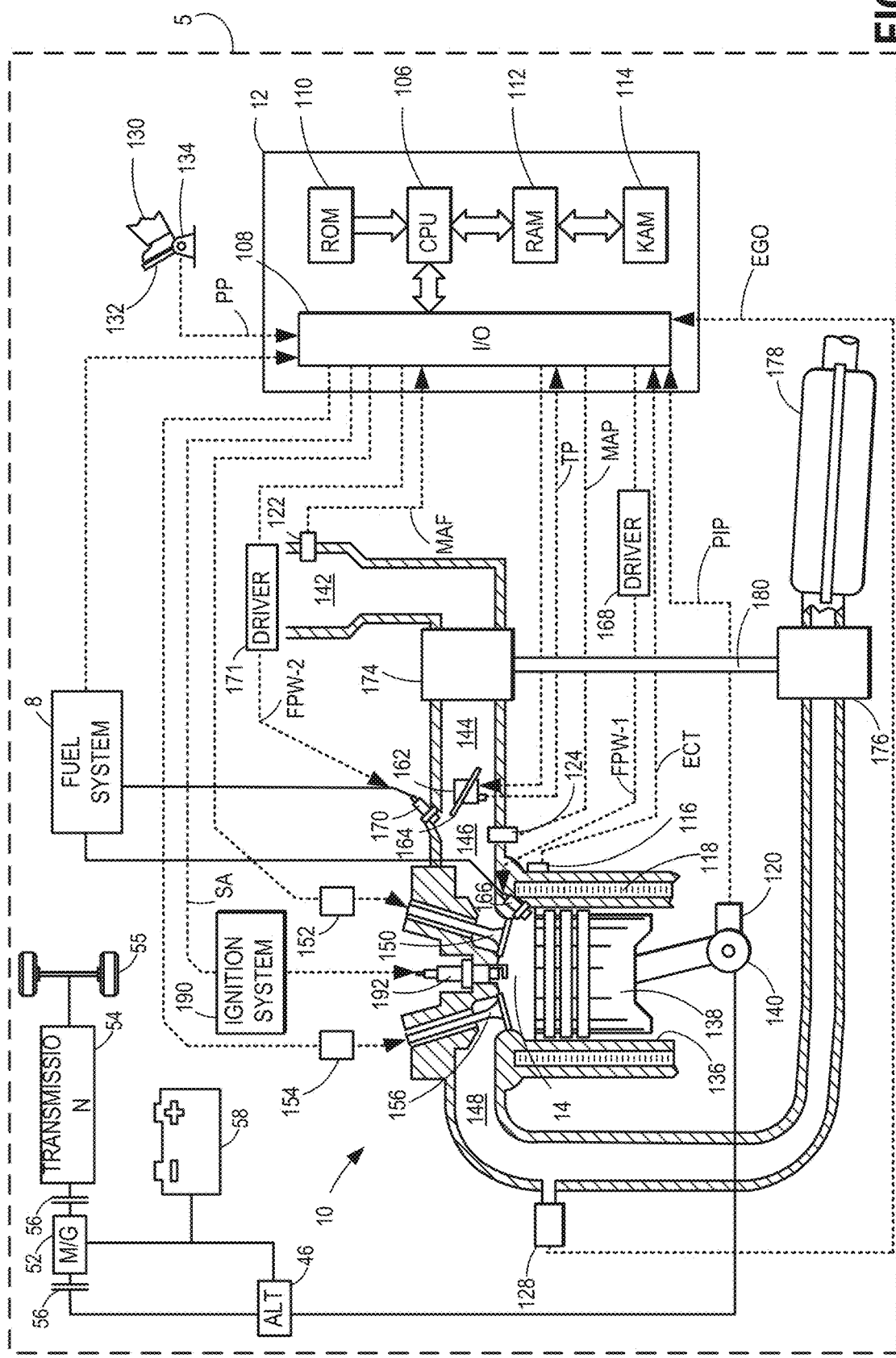
FIG. 1 schematically depicts an example embodiment of a cylinder of an internal combustion engine coupled to a hybrid vehicle.
Figure 2:
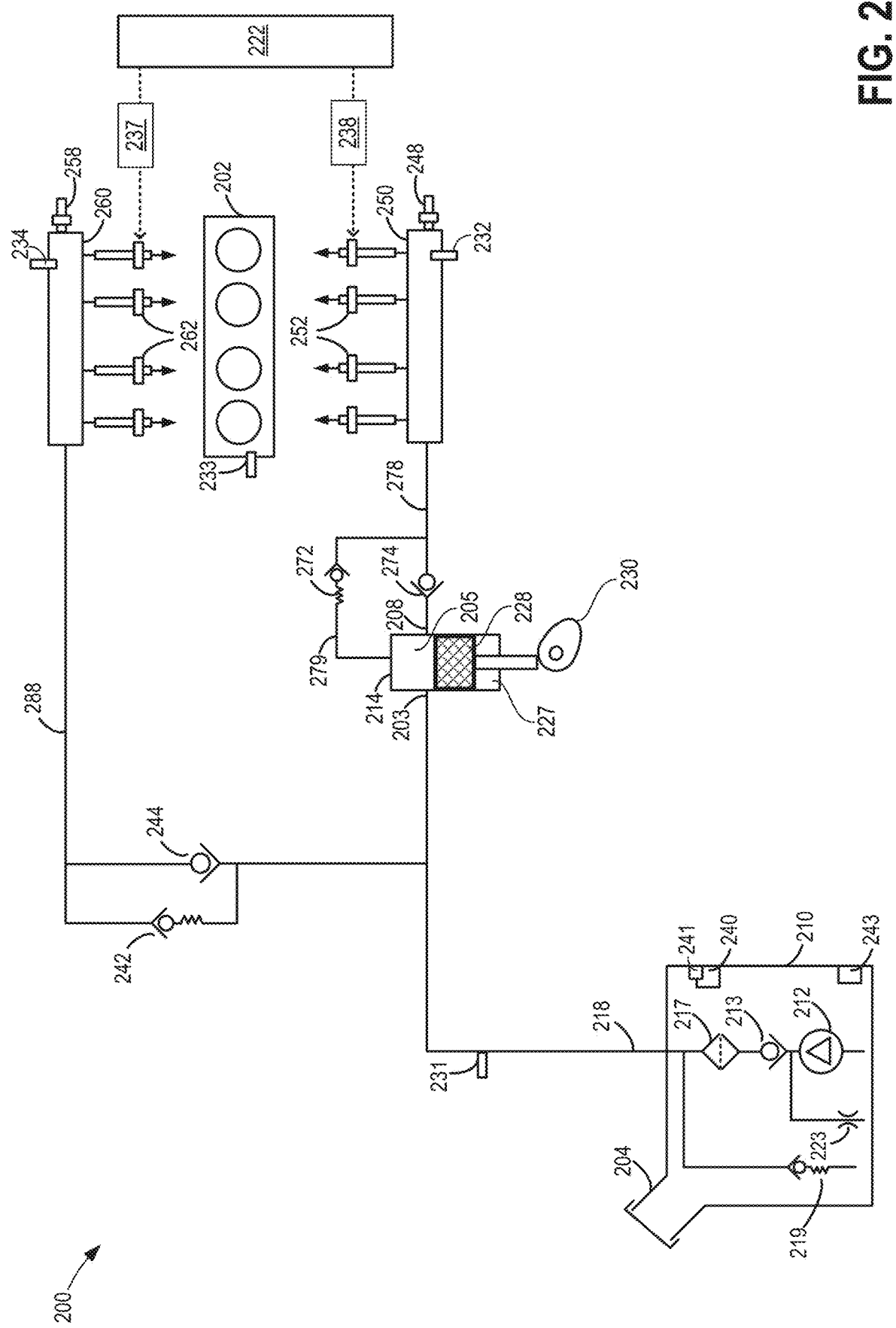
FIG. 2 schematically depicts an example embodiment of a fuel system, configured for port injection and direct injection that may be used with the engine of FIG. 1.

FIG. 1 depicts an example of a cylinder 14 of an internal combustion engine 10, which may be included in an engine system 100 in a vehicle 5. Engine 10 may be controlled at least partially by a control system including controller 12 and by input from a vehicle operator 130 via an input device 132. In this example, input device 132 includes an accelerator pedal and a pedal position sensor 134 for generating a proportional pedal position signal PP. Cylinder (herein also "combustion chamber") 14 of engine 10 may include combustion chamber walls 136 with piston 138 positioned therein. Piston 138 may be coupled to crankshaft 140 so that reciprocating motion of the piston is translated into rotational motion of the crankshaft. Crankshaft 140 may be coupled to at least one drive wheel of the passenger vehicle via a transmission system. Further, a starter motor (not shown) may be coupled to crankshaft 140 via a flywheel to enable a starting operation of engine 10.

Cylinder 14 can receive intake air via a series of intake air passages 142, 144, and 146. Intake air passage 146 can communicate with other cylinders of engine 10 in addition to cylinder 14. In some examples, one or more of the intake passages may include a boosting device such as a turbocharger or a supercharger. For example, FIG. 1 shows engine 10 configured with a turbocharger including a compressor 174 arranged between intake passages 142 and 144, and an exhaust turbine 176 arranged along exhaust passage 148. Compressor 174 may be at least partially powered by exhaust turbine 176 via a shaft 180 where the boosting device is configured as a turbocharger. However, in other examples, such as where engine 10 is provided with a supercharger, exhaust turbine 176 may be optionally omitted, where compressor 174 may be powered by mechanical input from a motor or the engine. A throttle 162 including a throttle plate 164 may be provided along an intake passage of the engine for varying the flow rate and/or pressure of intake air provided to the engine cylinders. For example, throttle 162 may be positioned downstream of compressor 174 as shown in FIG. 1, or alternatively may be provided upstream of compressor 174.

Exhaust passage 148 can receive exhaust gases from other cylinders of engine 10 in addition to cylinder 14. Exhaust gas sensor 128 is shown coupled to exhaust passage 148 upstream of emission control device 178. Sensor 128 may be selected from among various suitable sensors for providing an indication of exhaust gas air/fuel ratio such as a linear oxygen sensor or UEGO (universal or wide-range exhaust gas oxygen), a two-state oxygen sensor or EGO (as depicted), a HEGO (heated EGO), a NOx, HC, or CO sensor, for example. Emission control device 178 may be a three way catalyst (TWC), NOx trap, various other emission control devices, or combinations thereof.

Each cylinder of engine 10 may include one or more intake valves and one or more exhaust valves. For example, cylinder 14 is shown including at least one intake poppet valve 150 and at least one exhaust poppet valve 156 located at an upper region of cylinder 14. In some examples, each cylinder of engine 10, including cylinder 14, may include at least two intake poppet valves and at least two exhaust poppet valves located at an upper region of the cylinder.

Intake valve 150 may be controlled by controller 12 via actuator 152. Similarly, exhaust valve 156 may be controlled by controller 12 via actuator 154. During some conditions, controller 12 may vary the signals provided to actuators 152 and 154 to control the opening and closing of the respective intake and exhaust valves. The position of intake valve 150 and exhaust valve 156 may be determined by respective valve position sensors (not shown). The valve actuators may be of the electric valve actuation type or cam actuation type, or a combination thereof. The intake and exhaust valve timing may be controlled concurrently or any of a possibility of variable intake cam timing, variable exhaust cam timing, dual independent variable cam timing or fixed cam timing may be used. Each cam actuation system may include one or more cams and may utilize one or more of cam profile switching (CPS), variable cam timing (VCT), variable valve timing (VVT) and/or variable valve lift (VVL) systems that may be operated by controller 12 to vary valve operation. For example, cylinder 14 may alternatively include an intake valve controlled via electric valve actuation and an exhaust valve controlled via cam actuation including CPS and/or VCT. In other examples, the intake and exhaust valves may be controlled by a common valve actuator or actuation system, or a variable valve timing actuator or actuation system.

Cylinder 14 can have a compression ratio, which is the ratio of volumes when piston 138 is at bottom center to top center. In one example, the compression ratio is in the range of 9:1 to 10:1. However, in some examples where different fuels are used, the compression ratio may be increased. This may happen, for example, when higher octane fuels or fuels with higher latent enthalpy of vaporization are used. The compression ratio may also be increased if direct injection is used due to its effect on engine knock.

In some examples, each cylinder of engine 10 may include a spark plug 192 for initiating combustion. Ignition system 190 can provide an ignition spark to combustion chamber 14 via spark plug 192 in response to spark advance signal SA from controller 12, under select operating modes. However, in some embodiments, spark plug 192 may be omitted, such as where engine 10 may initiate combustion by auto-ignition or by injection of fuel as may be the case with some diesel engines.

In some examples, each cylinder of engine 10 may be configured with one or more fuel injectors for providing fuel thereto. As a non-limiting example, cylinder 14 is shown including two fuel injectors 166 and 170. Fuel injectors 166 and 170 may be configured to deliver fuel received from fuel system 8. As elaborated with reference to FIG. 2, the fuel system 8 may include one or more fuel tanks, fuel pumps, fuel rails, and fuel rail sensors. Fuel injector 166 is shown coupled directly to cylinder 14 for injecting fuel directly therein in proportion to the pulse width of signal FPW-1 received from controller 12 via electronic driver 168. In this manner, fuel injector 166 provides what is known as direct injection (hereafter referred to as "DI") of fuel into combustion cylinder 14. While FIG. 1 shows injector 166 positioned to one side of cylinder 14, it may alternatively be located overhead of the piston, such as near the position of spark plug 192. Such a position may improve mixing and combustion when operating the engine with an alcohol-based fuel due to the lower volatility of some alcohol-based fuels. Alternatively, the injector may be located overhead and near the intake valve to improve mixing. Fuel may be delivered to fuel injector 166 from a fuel tank of fuel system 8 via a high pressure fuel pump, and a fuel rail. Further, the fuel rail may have a pressure sensor and a temperature sensor providing a signal to controller 12.

Fuel injector 170 is shown arranged in intake passage 146, rather than in cylinder 14, in a configuration that provides what is known as port injection of fuel (hereafter referred to as "PFI") into the intake port upstream of cylinder 14. Fuel injector 170 may inject fuel, received from fuel system 8, in proportion to the pulse width of signal FPW-2 received from controller 12 via electronic driver 171. Note that a single driver 168 or 171 may be used for both fuel injection systems, or multiple drivers, for example driver 168 for fuel injector 166 and driver 171 for fuel injector 170, may be used, as depicted.

In an alternate example, each of fuel injectors 166 and 170 may be configured as direct fuel injectors for injecting fuel directly into cylinder 14. In still another example, each of fuel injectors 166 and 170 may be configured as port fuel injectors for injecting fuel upstream of intake valve 150. In yet other examples, cylinder 14 may include only a single fuel injector that is configured to receive different fuels from the fuel systems in varying relative amounts as a fuel mixture, and is further configured to inject this fuel mixture either directly into the cylinder as a direct fuel injector or upstream of the intake valves as a port fuel injector. As such, it should be appreciated that the fuel systems described herein should not be limited by the particular fuel injector configurations described herein by way of example.

Fuel may be delivered by both injectors to the cylinder during a single cycle of the cylinder. For example, each injector may deliver a portion of a total fuel injection that is combusted in cylinder 14. Further, the distribution and/or relative amount of fuel delivered from each injector may vary with operating conditions, such as engine load, knock, and exhaust temperature, such as described herein below. The port injected fuel may be delivered during an open intake valve event, closed intake valve event (e.g., substantially before the intake stroke), as well as during both open and closed intake valve operation. Similarly, directly injected fuel may be delivered during an intake stroke, as well as partly during a previous exhaust stroke, during the intake stroke, and partly during the compression stroke, for example. As such, even for a single combustion event, injected fuel may be injected at different timings from the port and direct injector. Furthermore, for a single combustion event, multiple injections of the delivered fuel may be performed per cycle. The multiple injections may be performed during the compression stroke, intake stroke, or any appropriate combination thereof.

Fuel injectors 166 and 170 may have different characteristics. These include differences in size, for example, one injector may have a larger injection hole than the other. Other differences include, but are not limited to, different spray angles, different operating temperatures, different targeting, different injection timing, different spray characteristics, different locations etc. Moreover, depending on the distribution ratio of injected fuel among injectors 170 and 166, different effects may be achieved.

Fuel tanks in fuel system 8 may hold fuels of different fuel types, such as fuels with different fuel qualities and different fuel compositions. The differences may include different alcohol content, different water content, different concentrations of lighter and heavier hydrocarbon ends, different octane, different heats of vaporization, different fuel blends, and/or combinations thereof etc. One example of fuels with different heats of vaporization could include gasoline as a first fuel type with a lower heat of vaporization and ethanol as a second fuel type with a greater heat of vaporization. In another example, the engine may use a flexible fuel containing alcohol such as E85 (which is approximately 85% ethanol and 15% gasoline) or M85 (which is approximately 85% methanol and 15% gasoline) as a second fuel type. Other feasible substances include water, methanol, a mixture of alcohol and water, a mixture of water and ethanol, a mixture of alcohols, etc.

In still another example, both fuels may be alcohol blends with varying alcohol composition wherein the first fuel type may be a gasoline alcohol blend with a lower concentration of alcohol, such as E10 (which is approximately 10% ethanol), while the second fuel type may be a gasoline alcohol blend with a greater concentration of alcohol, such as E85 (which is approximately 85% ethanol). Additionally, the first and second fuels may also differ in other fuel qualities such as a difference in temperature, viscosity, octane number, etc. Moreover, fuel characteristics of one or both fuel tanks may vary frequently, for example, due to day to day variations in tank refilling.

Controller 12 is shown in FIG. 1 as a microcomputer, including microprocessor unit 106, input/output ports 108, an electronic storage medium for executable programs and calibration values shown as non-transitory read only memory chip 110 in this particular example for storing executable instructions, random access memory 112, keep alive memory 114, and a data bus. Controller 12 may receive various signals from sensors coupled to engine 10, in addition to those signals previously discussed, including measurement of inducted mass air flow (MAF) from mass air flow sensor 122; engine coolant temperature (ECT) from temperature sensor 116 coupled to cooling sleeve 118; a profile ignition pickup signal (PIP) from Hall effect sensor 120 (or other type) coupled to crankshaft 140; throttle position (TP) from a throttle position sensor; absolute manifold pressure signal (MAP) from sensor 124; fuel rail pressure from a fuel rail pressure sensor; fuel rail temperature from a fuel rail temperature sensor; and ultrasonic signal amplitude from an ultrasonic signal sensor. Engine speed signal, RPM, may be generated by controller 12 from signal PIP. Manifold pressure signal MAP from a manifold pressure sensor may be used to provide an indication of vacuum, or pressure, in the intake manifold. The controller 12 receives signals from the various sensors of FIG. 1 and employs the various actuators of FIG. 1 to adjust engine operation based on the received signals and instructions stored on a memory of the controller.

As described above, FIG. 1 shows only one cylinder of a multi-cylinder engine. As such, each cylinder may similarly include its own set of intake/exhaust valves, fuel injector(s), spark plug, etc. It will be appreciated that engine 10 may include any suitable number of cylinders, including 2, 3, 4, 5, 6, 8, 10, 12, or more cylinders. Further, each of these cylinders can include some or all of the various components described and depicted by FIG. 1 with reference to cylinder 14.

In some examples, vehicle 5 may be a hybrid vehicle with multiple sources of torque available to one or more vehicle wheels 55. In other examples, vehicle 5 is a conventional vehicle with only an engine, or an electric vehicle with only electric machine(s). In the example shown, vehicle 5 includes engine 10 and an electric machine 52. Electric machine 52 may be a motor or a motor/generator. Crankshaft 140 of engine 10 and electric machine 52 are connected via a transmission 54 to vehicle wheels 55 when one or more clutches 56 are engaged. In the depicted example, a first clutch 56 is provided between crankshaft 140 and electric machine 52, and a second clutch 56 is provided between electric machine 52 and transmission 54. Controller 12 may send a signal to an actuator of each clutch 56 to engage or disengage the clutch, so as to connect or disconnect crankshaft 140 from electric machine 52 and the components connected thereto, and/or connect or disconnect electric machine 52 from transmission 54 and the components connected thereto. Transmission 54 may be a gearbox, a planetary gear system, or another type of transmission. The powertrain may be configured in various manners including as a parallel, a series, or a series-parallel hybrid vehicle.

Electric machine 52 receives electrical power from a traction battery 58 to provide torque to vehicle wheels 55. Electric machine 52 may also be operated as a generator to provide electrical power to charge battery 58, for example during a braking operation.

FIG. 2 schematically depicts an example embodiment 200 of a fuel system, such as fuel system 8 of FIG. 1. Fuel system 200 may be operated to deliver fuel to an engine, such as engine 10 of FIG. 1.

Fuel system 200 includes a fuel storage tank 210 for storing the fuel on-board the vehicle, a lower pressure fuel pump (LPP) 212, and a higher pressure fuel pump (HPP) 214 (herein also referred to as fuel pump 214). Fuel may be provided to fuel tank 210 via fuel filling passage 204. In one example, LPP 212 may be an electrically-powered lower pressure fuel pump disposed at least partially within fuel tank 210. LPP 212 may be operated by a controller 222 (e.g., controller 12 of FIG. 1) to provide fuel to HPP 214 via fuel passage 218. LPP 212 can be configured as what may be referred to as a fuel lift pump. As one example, LPP 212 may be a turbine (e.g., centrifugal) pump including an electric (e.g., DC) pump motor, whereby the pressure increase across the pump and/or the volumetric flow rate through the pump may be controlled by varying the electrical power provided to the pump motor, thereby increasing or decreasing the motor speed. For example, as the controller reduces the electrical power that is provided to lift pump 212, the volumetric flow rate and/or pressure increase across the lift pump may be reduced. The volumetric flow rate and/or pressure increase across the pump may be increased by increasing the electrical power that is provided to lift pump 212. As one example, the electrical power supplied to the lower pressure pump motor can be obtained from an alternator or other energy storage device on-board the vehicle (not shown), whereby the control system can control the electrical load that is used to power the lower pressure pump. Thus, by varying the voltage and/or current provided to the lower pressure fuel pump, the flow rate and pressure of the fuel provided at the inlet of the higher pressure fuel pump 214 is adjusted.

LPP 212 may be fluidly coupled to a filter 217, which may remove small impurities contained in the fuel that could potentially damage fuel handling components. A check valve 213, which may facilitate fuel delivery and maintain fuel line pressure, may be positioned fluidly upstream of filter 217. With check valve 213 upstream of the filter 217, the compliance of low-pressure passage 218 may be increased since the filter may be physically large in volume. Furthermore, a pressure relief valve 219 may be employed to limit the fuel pressure in low-pressure passage 218 (e.g., the output from lift pump 212). Relief valve 219 may include a ball and spring mechanism that seats and seals at a specified pressure differential, for example. The pressure differential set-point at which relief valve 219 may be configured to open may assume various suitable values; as a non-limiting example the set-point may be 6.4 bar or 5 bar (g). An orifice 223 may be utilized to allow for air and/or fuel vapor to bleed out of the lift pump 212. This bleed at orifice 223 may also be used to power a jet pump used to transfer fuel from one location to another within the tank 210. In one example, an orifice check valve (not shown) may be placed in series with orifice 223. In some embodiments, fuel system 8 may include one or more (e.g., a series) of check valves fluidly coupled to low-pressure fuel pump 212 to impede fuel from leaking back upstream of the valves. In this context, upstream flow refers to fuel flow traveling from fuel rails 250, 260 towards LPP 212 while downstream flow refers to the nominal fuel flow direction from the LPP towards the HPP 214 and thereon to the fuel rails.

Fuel lifted by LPP 212 may be supplied at a lower pressure into a fuel passage 218 leading to an inlet 203 of HPP 214. HPP 214 may then deliver fuel into a first fuel rail 250 coupled to one or more fuel injectors of a first group of direct injectors 252 (herein also referred to as a first injector group). Fuel lifted by the LPP 212 may also be supplied to a second fuel rail 260 coupled to one or more fuel injectors of a second group of port injectors 262 (herein also referred to as a second injector group). HPP 214 may be operated to raise the pressure of fuel delivered to the first fuel rail above the lift pump pressure, with the first fuel rail coupled to the direct injector group operating with a high pressure. As a result, high pressure DI may be enabled while PFI may be operated at a lower pressure.

While each of first fuel rail 250 and second fuel rail 260 are shown dispensing fuel to four fuel injectors of the respective injector group 252, 262, it will be appreciated that each fuel rail 250, 260 may dispense fuel to any suitable number of fuel injectors. As one example, first fuel rail 250 may dispense fuel to one fuel injector of first injector group 252 for each cylinder of the engine while second fuel rail 260 may dispense fuel to one fuel injector of second injector group 262 for each cylinder of the engine. Controller 222 can individually actuate each of the port injectors 262 via a port injection driver 237 and actuate each of the direct injectors 252 via a direct injection driver 238. The controller 222, the drivers 237, 238 and other suitable engine system controllers can comprise a control system. While the drivers 237, 238 are shown external to the controller 222, it should be appreciated that in other examples, the controller 222 can include the drivers 237, 238 or can be configured to provide the functionality of the drivers 237, 238. Controller 222 may include additional components not shown, such as those included in controller 12 of FIG. 1.

HPP 214 may be an engine-driven, positive-displacement pump. As one non-limiting example, HPP 214 may be a BOSCH HDP5 HIGH PRESSURE PUMP, which utilizes a solenoid activated control valve (e.g., fuel volume regulator, magnetic solenoid valve, etc.) to vary the effective pump volume of each pump stroke. The outlet check valve of HPP is mechanically controlled and not electronically controlled by an external controller. HPP 214 may be mechanically driven by the engine in contrast to the motor driven LPP 212. HPP 214 includes a pump piston 228, a pump compression chamber 205 (herein also referred to as compression chamber), and a step-room 227. Pump piston 228 receives a mechanical input from the engine crank shaft or cam shaft via cam 230, thereby operating the HPP according to the principle of a cam-driven single-cylinder pump. A sensor (not shown in FIG. 2) may be positioned near cam 230 to enable determination of the angular position of the cam (e.g., between 0 and 360 degrees), which may be relayed to controller 222.

A lift pump fuel pressure sensor 231 may be positioned along fuel passage 218 between lift pump 212 and higher pressure fuel pump 214. In this configuration, readings from sensor 231 may be interpreted as indications of the fuel pressure of lift pump 212 (e.g., the outlet fuel pressure of the lift pump) and/or of the inlet pressure of higher pressure fuel pump. Readings from sensor 231 may be used to assess the operation of various components in fuel system 200, to determine whether sufficient fuel pressure is provided to higher pressure fuel pump 214 so that the higher pressure fuel pump ingests liquid fuel and not fuel vapor, and/or to minimize the average electrical power supplied to lift pump 212.

First fuel rail 250 includes a first fuel rail pressure sensor 248 and a first fuel rail temperature sensor 232 for providing an indication of direct injection fuel rail pressure and first fuel rail temperature, respectively, to the controller 222. Likewise, second fuel rail 260 includes a second fuel rail pressure sensor 258 and a first fuel rail temperature sensor 232 for providing an indication of port injection fuel rail pressure and second fuel rail temperature, respectively, to the controller 222.

The fuel rail pressure sensors 248 and/or 258 and the fuel rail temperature sensors 232 and/or 234 may be used to determine ethanol content and/or age of fuel in the fuel tank 210. For flexible fuels (containing ethanol), the fuel ethanol content is a percentage of ethanol in fuel contained in a fuel tank 210 of an engine fuel system For gasoline, fuel age is an indication of change in fuel constituents over time due to vaporization of the fuel's lighter, more volatile ends. The vaporized part of the fuel may be routed either to a fuel vapor storage canister or into the atmosphere. The fuel aging process is a function of duration and conditions (such as temperature variation during diurnal cycles) at which the fuel is stored in the fuel tank. In one example, if the fuel is stored at a higher temperature (such as during hot ambient conditions) for a longer duration, the vaporization process may be expedited, thereby increasing the fuel age. In a hybrid vehicle, the fuel age may be estimated periodically after completion of a threshold distance of travel and/or duration of travel since an immediately previous fuel age estimation. In a flex-fuel vehicle, the fuel ethanol content may be estimated periodically at least within a first threshold distance of travel and/or duration of travel after a refueling event and the fuel water content may be estimated periodically after completion of a second threshold distance of travel and/or duration of travel since an immediately previous fuel age estimation, the second threshold distance of travel and/or duration of travel being higher than the first threshold distance of travel and/or duration of travel.

A volume fraction of ethanol in fuel, a volume fraction of water in fuel, and an age of fuel contained in a fuel tank 210 may be estimated based on an estimated fuel rail temperature and one of a pulsation frequency, a change in pressure, and a damping coefficient of pressure pulsations as estimated after a fuel injection or a pump stroke. The change in pressure during a fuel pump stroke or fuel injection may be a function of the fuel bulk modulus, the damping coefficient of pressure pulsations in a fuel rail (such as first fuel rail 250) immediately after a fuel pump stroke or fuel injection may be a function of the fuel viscosity, and the resonant frequency of the pressure pulsations in the fuel rail may be a function of the speed of sound in fuel. In response to the estimation of the fuel ethanol content, water content, and fuel age, one or more engine operating parameters may be adjusted. As an example, the amount of injected fuel during a cold start may be increased in response to an increase in ethanol volume fraction or an increase in fuel age, and the commanded air-fuel ratio may be decreased in response to an increase in ethanol volume fraction, and spark timing may be advanced in response to an increase in ethanol volume fraction. Methods for fuel ethanol content, water content, and/or aging determination is discussed in details with reference to FIGS. 3-6.

In an alternate embodiment, fuel rail temperature sensors 232 and 234 may be eliminated and fuel rail temperature may be determined based on fuel rail pressure variations. If fuel rail temperature is not known, such as in a port injection system without a fuel rail temperature sensor, the volume fractions of ethanol and water in fuel and the fuel rail temperature may be estimated in a flex fuel vehicle based on at least three of a pulsation frequency, a change in pressure, and a damping coefficient of pressure pulsations as estimated after a fuel injection or a pump stroke. In a hybrid vehicle, the fuel age and the fuel rail temperature may be estimated based on at least two of the pulsation frequency, a change in pressure, and a damping coefficient of pressure pulsations as estimated after a fuel injection or a pump stroke. Methods for fuel rail temperature determination is discussed in details with reference to FIGS. 5-6.

An engine speed sensor 233 can be used to provide an indication of engine speed to the controller 222. The indication of engine speed can be used to identify the speed of higher pressure fuel pump 214, since the pump 214 is mechanically driven by the engine 202, for example, via the crankshaft or camshaft.

First fuel rail 250 is coupled to an outlet 208 of HPP 214 along fuel passage 278. A check valve 274 and a pressure relief valve (also known as pump relief valve) 272 may be positioned between the outlet 208 of the HPP 214 and the first (DI) fuel rail 250. The pump relief valve 272 may be coupled to a bypass passage 279 of the fuel passage 278. Outlet check valve 274 opens to allow fuel to flow from the high pressure pump outlet 208 into a fuel rail only when a pressure at the outlet of direct injection fuel pump 214 (e.g., a compression chamber outlet pressure) is higher than the fuel rail pressure. The pump relief valve 272 may limit the pressure in fuel passage 278, downstream of HPP 214 and upstream of first fuel rail 250. For example, pump relief valve 272 may limit the pressure in fuel passage 278 to 200 bar. Pump relief valve 272 allows fuel flow out of the DI fuel rail 250 toward pump outlet 208 when the fuel rail pressure is greater than a predetermined pressure. Valves 244 and 242 work in conjunction to keep the low pressure fuel rail 260 pressurized to a pre-determined low pressure. Pressure relief valve 242 helps limit the pressure that can build in fuel rail 260 due to thermal expansion of fuel.

Based on engine operating conditions, fuel may be delivered by one or more port injectors 262 and direct injectors 252. For example, during high load conditions, fuel may be delivered to a cylinder on a given engine cycle via only direct injection, wherein port injectors 262 are disabled. In another example, during mid load conditions, fuel may be delivered to a cylinder on a given engine cycle via each of direct and port injection. As still another example, during low load conditions, engine starts, as well as warm idling conditions, fuel may be delivered to a cylinder on a given engine cycle via only port injection, wherein direct injectors 252 are disabled.

It is noted here that the high pressure pump 214 of FIG. 2 is presented as an illustrative example of one possible configuration for a high pressure pump. Components shown in FIG. 2 may be removed and/or changed while additional components not presently shown may be added to pump 214 while still maintaining the ability to deliver high-pressure fuel to a direct injection fuel rail and a port injection fuel rail.

In an alternate embodiment, the fuel system may include only the port injectors 262 instead of both direct injectors and port injectors 262. Also, in case of fuel injection via port injectors 262, the second fuel rail 260 may be eliminated. A fuel temperature sensor 243 may be housed in the fuel tank to facilitate estimation of fuel temperature in the tank. An ultrasonic signal generator 240 may be coupled to a wall of the fuel tank 210, and an ultrasonic sensor 241 may be coupled to the generator 240. The ultrasonic signal generator 240 may generate ultrasonic waves which may pass through the fuel in the tank. The waves may get reflected from a fixed object such as a wall of the tank opposite to the wall on which the signal generator 240 is mounted. In this way, the ultrasonic signal may be generated by an ultrasonic signal generator coupled to a first wall of a fuel tank, and the ultrasonic signal may be detected by an ultrasonic sensor coupled to the first wall, adjacent to the ultrasonic signal generator, each of the ultrasonic signal generator and the ultrasonic sensor being immersed in fuel. A speed of sound in fuel may be estimated based on a time of travel of a reflected ultrasonic signal to and from a second wall, opposite to the first wall, and a distance between the first wall and the second wall. Also, an attenuation co-efficient of ultrasonic signal in fuel may be estimated based on a difference in amplitude between the generated ultrasonic signal and the reflected ultrasonic signal. A volume fraction of ethanol in fuel or an age of the fuel contained in the fuel tank may be estimated based on each of the fuel temperature, the speed of sound in the fuel, and the attenuation co-efficient of ultrasonic signal in the fuel. Methods for fuel ethanol content and/or aging determination using an ultrasonic signal are discussed in details with reference to FIGS. 15-16.

Controller 222 can also control the operation of each of fuel pumps 212, and 214 to adjust an amount, pressure, flow rate, etc., of a fuel delivered to the engine. As one example, controller 222 can vary a pressure setting, a pump stroke amount, a pump duty cycle command and/or fuel flow rate of the fuel pumps to deliver fuel to different locations of the fuel system. A driver (not shown) electronically coupled to controller 222 may be used to send a control signal to the low pressure pump, as required, to adjust the output (e.g., speed, flow output, and/or pressure) of the low pressure pump.

In this way, the systems discussed above at FIGS. 1 and 2 may enable an engine system comprising: a controller with computer readable instructions stored on non-transitory memory that, when executed, cause the controller to: upon completion of a refueling event, estimate a fuel ethanol and water content based on each of a temperature of a fuel rail and two fuel rail pressure factors, and adjust one or more of amount of injected fuel and spark timing, based on the estimated fuel ethanol and water content, or upon completion of a threshold duration since an immediately prior fuel age estimation, estimate fuel age based on each of the temperature of the fuel rail and the fuel rail pressure factor, and adjust one or more of amount of injected fuel and fuel injection timing. The fuel rail pressure factor may include one or more of a change in fuel rail pressure responsive to a stroke of a fuel pump or fuel injection, a damping coefficient of pressure pulsations in a fuel rail immediately after the stroke or injection, and a resonant frequency of the pressure pulsations in the fuel rail immediately after the stroke or injection.

Figure 3:
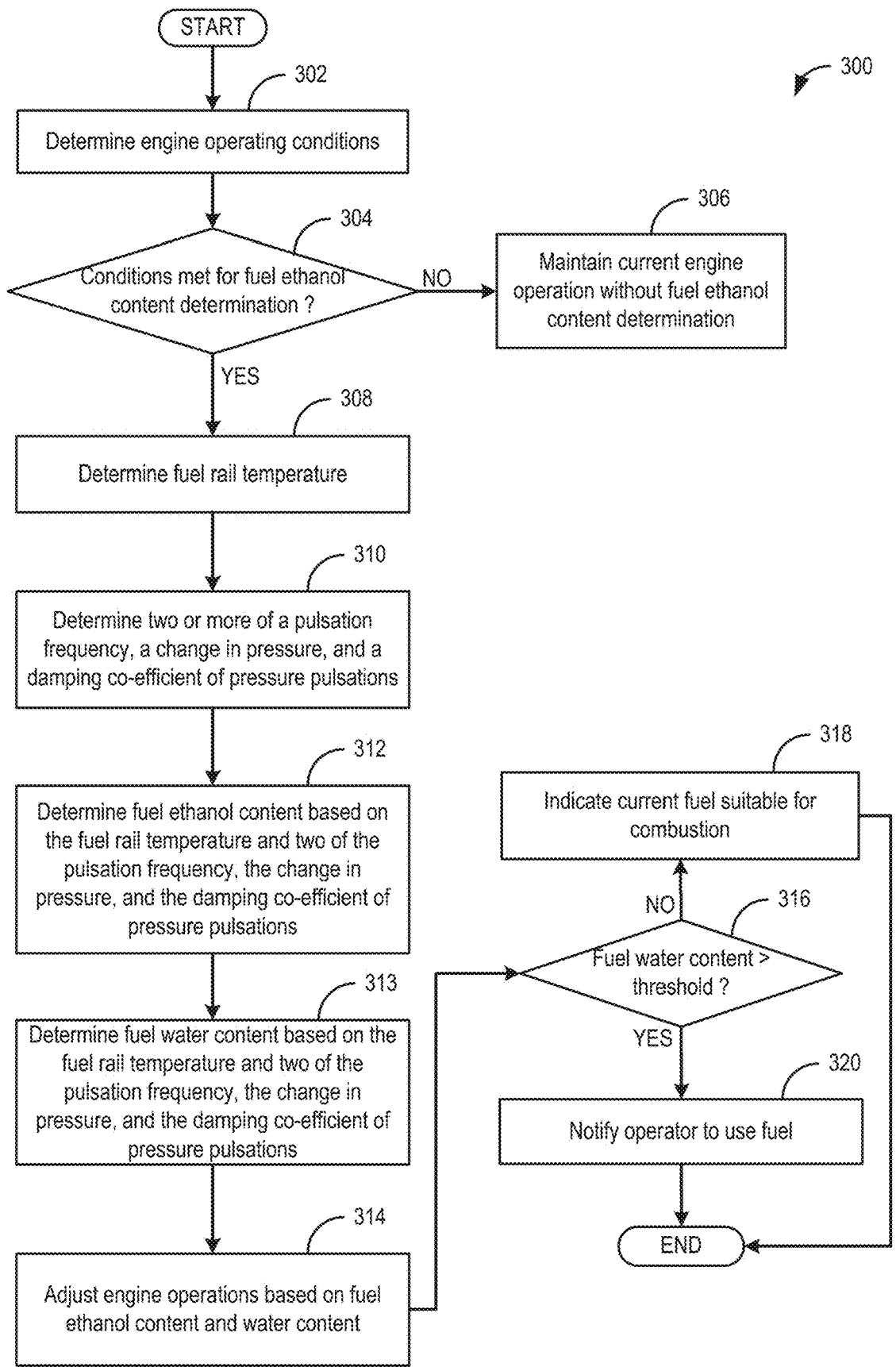
FIG. 3 shows a flow chart illustrating a first method for determining ethanol content in a flex-fuel powered vehicle.

FIG. 3 shows an example method 300 that can be implemented to estimate a volume fraction of ethanol and water in fuel. Instructions for carrying out method 300 and the rest of the methods included herein may be executed by a controller based on instructions stored on a memory of the controller and in conjunction with signals received from sensors of the engine system, such as the sensors described above with reference to FIGS. 1 and 2. The controller may employ engine actuators of the engine system to adjust engine operation, according to the methods described below.

At 302, current vehicle and engine operating parameters may be determined. The parameters may include vehicle speed, torque demand, engine speed, engine temperature, etc. The controller may estimate an amount of fuel supplied to the fuel injectors (direct injectors and/or port injectors) via the first fuel rail (such as first fuel rail 250 in FIG. 2) coupled to the direct injectors (such as direct injectors 252 in FIG. 2) and the second fuel rail (such as second fuel rail 260 in FIG. 2) coupled to the port injectors (such as port injectors 262 in FIG. 2). The controller may monitor operation of a fuel pump (such as high pressure pump 214 in FIG. 2) such as timing of a fuel pump stroke.

At 304, the routine includes determining if conditions are met for fuel ethanol content determination. Ethanol content determination may be carried out in an engine using a flexible fuel containing ethanol (such as E85 containing 85% ethanol). Thus, in some examples, the ethanol content determination may be carried out only in vehicles configured to operate with ethanol fuel (e.g., flex fuel vehicles). In one example, ethanol content estimation may be carried out after a vehicle refueling is detected.

The conditions may include the vehicle being propelled via engine torque with fuel being supplied to the injectors via a fuel rail (such as the first fuel rail). The conditions may further include a refueling event having occurred within a threshold amount of time. During refueling with a fuel that may contain ethanol, fuel remaining in the fuel tank may mix with the fuel that is being dispensed, resulting in a fuel blend of existing and new fuel. The ethanol content and the water content of the fuel blend may be different from the ethanol content and water content of the existing fuel or the delivered fuel, and the ethanol content of the fuel blend may be estimated within a threshold duration (or a threshold distance of travel) after the refueling event. For example, such estimations may be carried out within 1 day of refueling or within 10 miles of travel after refueling. Due to the amount of water absorbed by ethanol may change over time (between refueling events), the conditions may further include a threshold duration of time elapsing since a prior fuel ethanol content estimation. For example, such estimations may be carried out periodically, such as every 15 days. If it is determined that conditions are not met for fuel ethanol content determination, at 306, current engine operation may be continued without fuel ethanol content determination. Engine operation may include supplying fuel to one or more fuel injectors via one or more fuel rails.

If it is determined that conditions are met for fuel ethanol content determination, at 308, fuel rail temperature may be estimated via a fuel rail temperature sensor (such as first fuel rail temperature sensor 232 in FIG. 2) coupled to the fuel rail. Alternatively, fuel rail temperature may be estimated using a physics-based or empirical model relating fuel rail temperature to the engine operating conditions and states.

At 310, two or more of a resonant frequency (f) of pressure pulsations, a change in fuel rail pressure ($\delta p$), and a damping coefficient ($\alpha$) of pressure pulsations in the fuel rail may be estimated after a fuel injection or a pump stroke. In one example, fuel bulk modulus may be estimated based on a function of the change in fuel rail pressure ($\delta p$) caused by a pump stroke or injection event, a speed of sound in fuel may be estimated based on a function of the resonant frequency (f) of pressure pulsations in the fuel rail due to a fuel pump stroke or a fuel injection and a fuel viscosity may be estimated based on a function of the damping coefficient ($\alpha$) of pressure pulsations in the fuel rail after a fuel pump stroke or a fuel injection.

In order to estimate one or more of the change in fuel rail pressure ($\delta p$), resonant frequency (f) of pressure pulsations, and a damping coefficient ($\alpha$) of pressure pulsations, a pump stroke of a high pressure fuel pump (such as HP fuel pump 214 in FIG. 2) housed in a fuel tank may be determined. The pump stroke may correspond to operation of the pump to deliver fuel from the fuel tank to the direct injector fuel rail via a fuel line. A change (increase) in fuel rail pressure may be determined via fuel rail pressure sensors (such as pressure sensor 248 in FIG. 2) immediately after the pump stroke. As the pump is operated to transfer fuel from the fuel tank to the fuel rail, the fuel rail pressure may increase during a pump stroke. As an example, during the pump stroke, the controller may estimate a change in a magnitude of pressure or a slope of pressure.

The controller may determine a fuel direct injection event that results in at least a threshold change (decrease) in the amount of fuel remaining in the rail. Fuel may be injected via one or more direct injectors (such as direct injectors 252) coupled to a fuel rail. A duration of fuel injection may be estimated. The duration may include a time elapsed between a start of fuel injection to a completion of fuel injection to a certain cylinder at a single fuel injection event. Fuel may be pumped from the fuel tank to the direct injectors via the fuel line and rail. The decrease in the amount of fuel remaining in the rail following the injection event may result in a decrease in the fuel rail pressure. A change (decrease) in fuel rail pressure may be determined via fuel rail pressure sensors (such as pressure sensor 248 in FIG. 2) immediately after the fuel injection. In this way, a change in fuel rail pressure may be estimated immediately after a fuel injection or a fuel pump stroke.

After the pump stroke or fuel injection, pressure pulsations may be generated at the fuel rail. The fuel rail pulsations may have a resonant frequency. The resonant frequency of pressure pulsations in the fuel rail may be determined via processing the pressure signal from fuel rail pressure sensors (such as pressure sensor 248 in FIG. 2) after the pump stroke or fuel injection.

The pressure pulsations generated at the fuel rail after the fuel injection or the pump stroke may be damped with the amplitude of the pulsations decreasing over time. The amplitude of the pressure pulsations may decay at an exponential rate. A damping coefficient of the pressure pulsations in the fuel rail may be determined. An exponential curve may be fit to the decaying amplitude profile of the pressure pulsations and/or an exponential function may be fit to the pressure signal envelope. In one example, the damping coefficient may be a constant in the exponential function. In another example, an exponentially damped sinusoid curve may be fitted to the decaying pressure pulsations. The damping coefficient may be a constant in the exponential function (multiplied by the sinusoid). In yet another example, the damping coefficient may be estimated using Prony analysis. The Fast Fourier Transform (FFT) of the pressure signal may also be used for estimating the damping coefficient as amplitude of the resonant frequency component obtained from FFT is a function of the damping coefficient.

Figure 7:
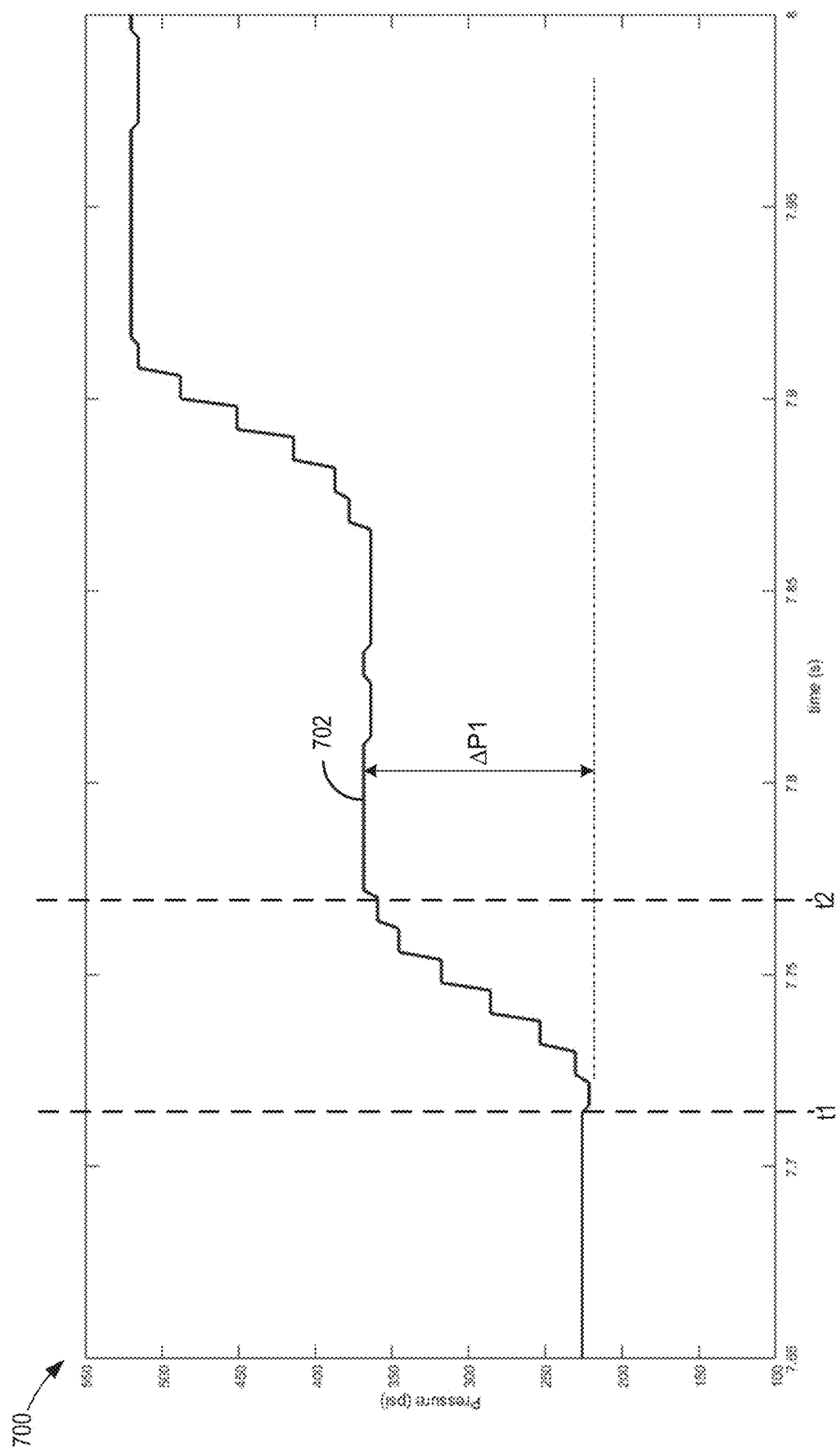
FIG. 7 shows a plot illustrating change in fuel rail pressure in response to a fuel pump stroke.

FIG. 7 shows an example plot 700 illustrating a change in fuel rail pressure over time. The y-axis denotes fuel rail pressure (in psi) and the x-axis denotes time in (sec). The pressure may be estimated via a pressure sensor coupled to the fuel rail (such as pressure sensor 248 in FIG. 2).

At time t1, a fuel pump stroke may begin and continue until time t2. Between time t1 and t2, as shown by line 702, there is a steady increase in fuel tank pressure. After the completion of the pump stroke, the pressure may plateau. The difference in pressure (AP1) between the pressure at time t1 and the pressure at time t2 may be the change in fuel rail pressure immediately following a fuel pump stroke. Also, the slope of the fuel rail pressure plot between time t1 and t2 may be estimated.

Figure 8:
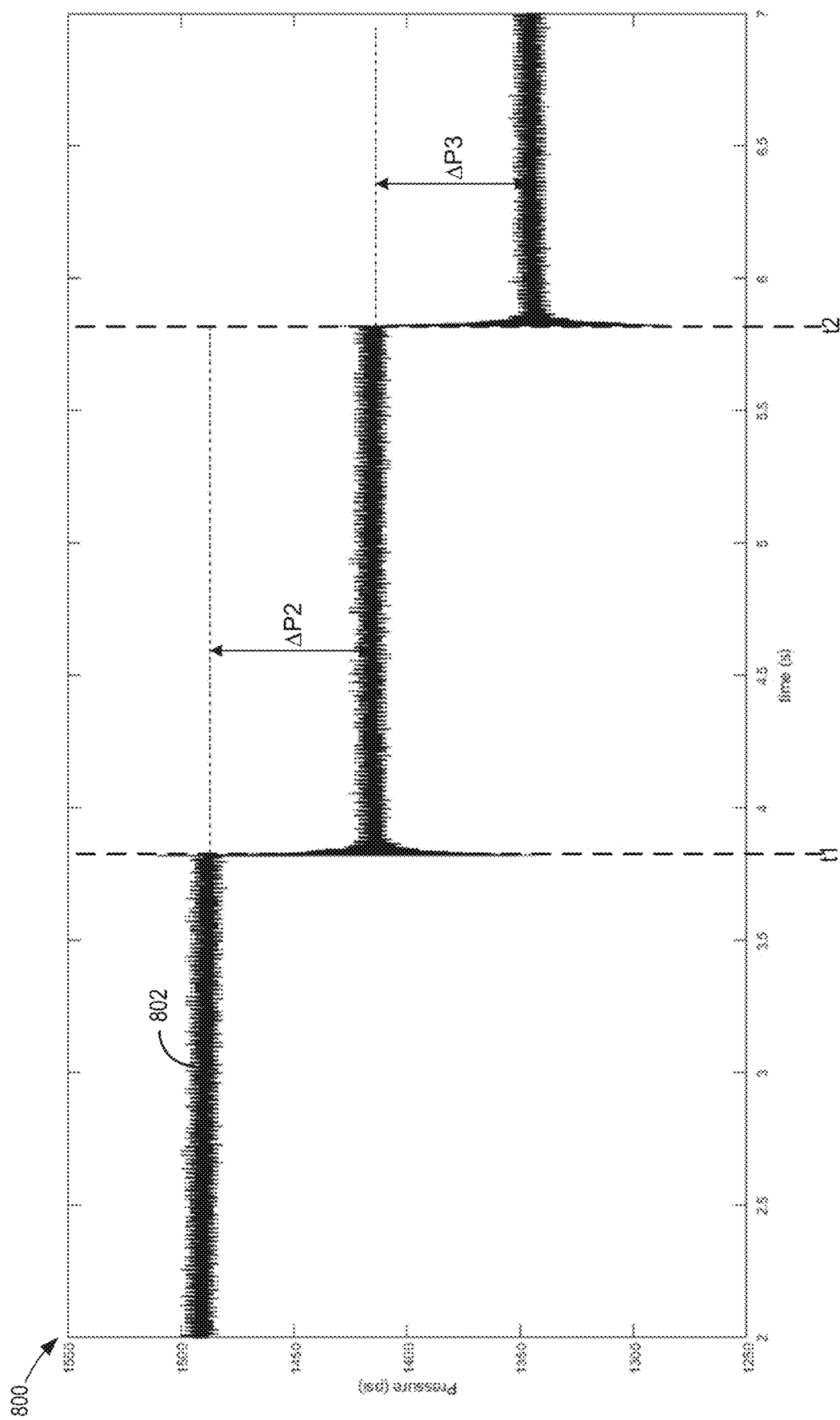
FIG. 8 shows a plot illustrating change in fuel rail pressure in response to a fuel injection.

FIG. 8 shows an example plot 800 illustrating a change in fuel rail pressure over time. The y-axis denotes fuel rail pressure (in psi) and the x-axis denotes time in (sec). The pressure may be estimated via a pressure sensor coupled to the fuel rail (such as pressure sensor 248 in FIG. 2). The plot is generated based on an experiment where the fuel injection duration is set at 2 ms.

A first fuel injection may take place at time t1 followed by a second fuel injection at time t2. As seen in line 802, ΔP2 may be the difference in fuel rail pressure immediately before and after the first fuel injection and ΔP3 may be the difference in fuel rail pressure immediately before and after the second fuel injection.

Figure 9:
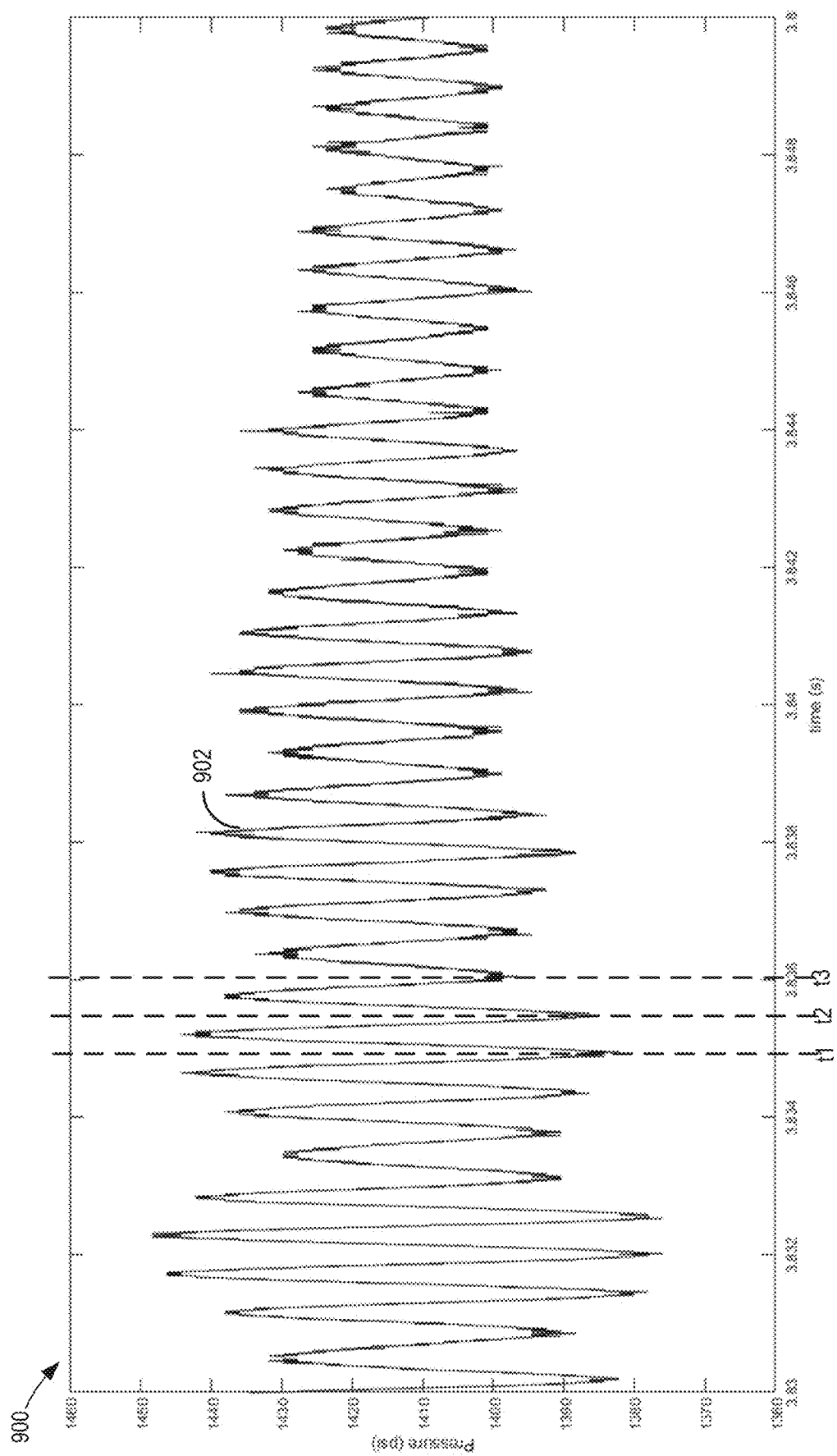
FIG. 9 shows a plot illustrating resonant pulsations in fuel rail pressure in response to a fuel injection.

FIG. 9 shows an example plot 900 illustrating resonant frequency pulsations in the fuel rail after a pump stroke. The y-axis denotes fuel rail pressure (in psi) and the x-axis denotes time in (sec). The pressure may be estimated via a pressure sensor coupled to the fuel rail (such as pressure sensor 248 in FIG. 2). As seen in line 902, pressure pulsations troughs occur at time t1, t2, t3, etc. The frequency may be determined using Fast Fourier Transform (FFT) or Prony analysis.

Figure 10:
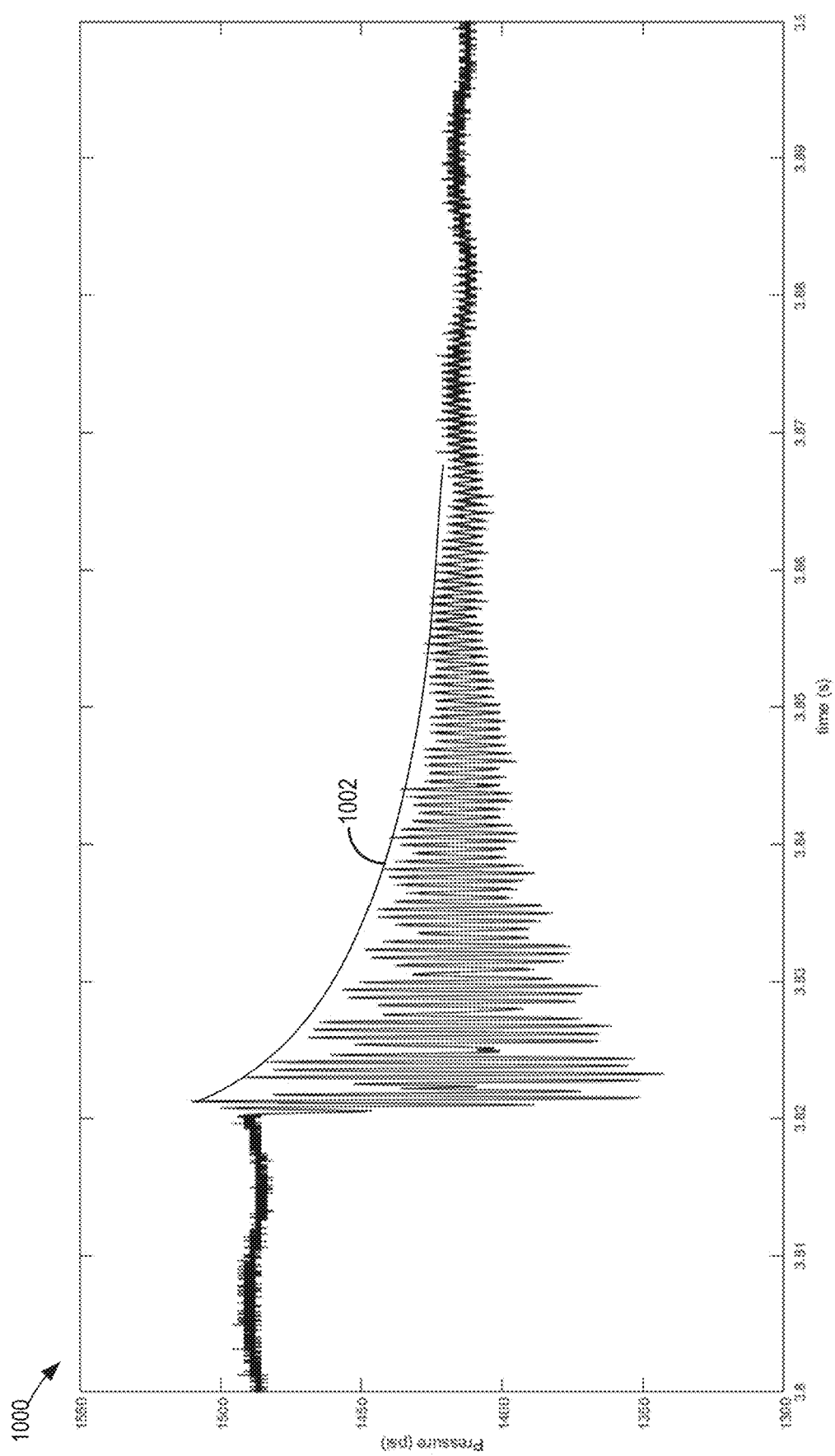
FIG. 10 shows a plot illustrating damping of pressure pulsations in fuel rail after a fuel injection.

FIG. 10 shows an example plot 1000 illustrating damping of pressure pulsations in the fuel rail after a fuel injection. The y-axis denoted fuel rail pressure (in psi) and the x-axis denotes time (in sec). The pressure may be estimated via a pressure sensor coupled to the fuel rail (such as pressure sensor 248 in FIG. 2). As seen in line 1002, an exponential curve may be fit to the decaying amplitudes of the pressure pulsations. The damping coefficient may be estimated based on the exponential function of the fitted curve. The damping coefficient may also be estimated based on the exponential function of a damped sinusoid curve, or using Prony analysis, or FFT.

At 312, fuel ethanol content (volume fraction) may be estimated based on the fuel rail temperature, the resonant frequency (f) of pressure pulsations, the change in fuel rail pressure (δp), and the damping coefficient (α) of pressure pulsations in the fuel rail as estimated after a fuel injection or a pump stroke. During conditions when fuel water content is not known, the fuel ethanol content may be estimated as a function of fuel rail temperature and two of the resonant frequency (f) of pressure pulsations, the change in fuel rail pressure (δp), and the damping coefficient (α) of pressure pulsations in the fuel rail. Said another way, the fuel ethanol content may be estimated based on the fuel rail temperature and at least two of the estimated fuel bulk modulus, the speed of sound in fuel, and the fuel viscosity. In one example, a first estimate of ethanol content may be computed as a function of the fuel rail temperature, f, and α, and a second estimate may be computed as a function of the fuel rail temperature, δp, and α. Ethanol content may then be estimated as a weighted average of the first and second estimates. A weighted average of the estimates from based on different functions may be used to improve accuracy.

During conditions when fuel water content is known fuel ethanol content may be estimated as one of a first function of resonant frequency (f) and fuel rail temperature, a second function of change in fuel rail pressure (δp) in fuel and fuel rail temperature, and as a third function of damping coefficient (α) and fuel rail temperature.

FIG. 11 shows an example plot 1100 depicting a relationship between ethanol content in fuel and a normalized root mean square (RMS) envelope of fuel rail pressure pulsations. The x-axis denotes time and the y-axis denotes a RMS envelope of rail pressure pulsations in fuel containing 0% ethanol, 50% ethanol, or 100% ethanol. As seen from the plot, since ethanol has higher viscosity relative to gasoline, the decay rate of the pressure pulsations becomes faster with an increase in fuel ethanol content.

FIG. 12 shows an example plot 1200 depicting a relationship between ethanol content in fuel and a damping coefficient (α) of fuel rail pressure pulsations. The x-axis denotes a measurement number and the y-axis denotes a damping coefficient (in Hz) in fuel containing 0% ethanol, 50% ethanol, or 100% ethanol. As seen from the plot, the damping coefficient increases with an increase in fuel ethanol content.

FIG. 13 shows an example plot 1300 depicting a relation between ethanol content in fuel and the speed of sound through fuel. The speed of sound may be estimated based on the resonant frequency (f) of pressure pulsations in fuel. The x-axis denotes ethanol volume fraction (%) in fuel and the y-axis shows a speed of sound (in m/s) in fuel. The speed of sound may change non-monotonically with the change in ethanol content. Up to an ethanol fraction of 30%, the speed of sound is inversely proportional to the ethanol fraction and above an ethanol fraction of 30%, the speed of sound is directly proportional to the ethanol fraction.

Returning to FIG. 3, at 312, the fuel ethanol content may be estimated directly based on two or more of the damping coefficient α of pressure pulsations, fuel rail pressure pulsation frequency f, change in fuel rail pressure during a pump stroke δp, fuel rail temperature T, and fuel rail pressure p. As an example, if water content is insignificant, damping coefficient α, fuel rail pressure pulsation frequency f, and change in fuel rail pressure during a pump stroke δp are a function of ethanol volume fraction y, fuel rail temperature T, & fuel rail pressure p: α=$f$(y,T,p), f=$g$(y,T,p), and δp=$h$(y,T,p)

A relationship between the above mentioned variables is given by:

$$\left\{ \begin{bmatrix} y_1 \\ \vdots \\ y_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \left\{ \begin{bmatrix} \alpha_1 \\ \vdots \\ \alpha_N \end{bmatrix}, \begin{bmatrix} f_1 \\ \vdots \\ f_N \end{bmatrix}, \begin{bmatrix} \delta p_1 \\ \vdots \\ \delta p_N \end{bmatrix} \right\}$$

where 1, 2, . . . N are the number of measurements (data points) of each of the variables. Inverse mapping $f^{-1}$, $g^{-1}$ and $h^{-1}$ such that $\hat{y}_a = f^{-1}(\alpha, T, p)$, $\hat{y}_f = g^{-1}(f,T,p)$ and $\hat{y}_{\delta p} = h^{-1}(\delta p, T, p)$ may be used to estimate the ethanol volume fraction. $f^{-1}$, $g^{-1}$ and $h^{-1}$ may be determined from a fit (plot) or a look-up table.

In this way, the ethanol volume fraction (y) may be determined using the relationships (1), (2) or (3):

$$\left\{ \begin{bmatrix} \alpha_1 \\ \vdots \\ \alpha_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \begin{bmatrix} \hat{y}_{\alpha 1} \\ \vdots \\ \hat{y}_{\alpha N} \end{bmatrix} \quad (1)$$

$$\left\{ \begin{bmatrix} f_1 \\ \vdots \\ f_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \begin{bmatrix} \hat{y}_{f1} \\ \vdots \\ \hat{y}_{fN} \end{bmatrix} \quad (2)$$

$$\left\{ \begin{bmatrix} \delta p_1 \\ \vdots \\ \delta p_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \begin{bmatrix} \hat{y}_{\delta p 1} \\ \vdots \\ \hat{y}_{\delta p N} \end{bmatrix} \quad (3)$$

If dependence on fuel rail pressure (p) is neglibible (such as less than 20), fuel rail pressure (p) may be dropped from the estimation and the ethanol volume fraction may be estimated as a function of damping coefficient (α) and fuel rail temperature (T) or a function of fuel rail pressure pulsation frequency (f) and and fuel rail temperature (T). Ethanol content (y) may be estimated as $\hat{y}_\alpha$, $\hat{y}_f$ or $\bar{y}_{\delta p}$, or a weighted average of $\hat{y}_\alpha$, $\hat{y}_f$ and $\hat{y}_{\delta p}$. Due to a non-monotonic behavior, the inverse mapping may give two possible ethanol contents. For example, a speed of sound of 1160 m/s can either correspond to an ethanol content of 9% or 90%. In this case, another parameter, e.g. damping coefficient, may be used to determine which of the two estimates based on the speed of sound is the correct one. For example, if the ethanol content estimated based on the damping coefficient is 10%, the 90% estimate may be ignored, and ethanol content may be estimated as a weighted average of 9% and 10%.

As another example, if water content is significant but not known, damping coefficient α, fuel rail pressure pulsation frequency f, and change in fuel rail pressure during a pump stroke δp are a function of ethanol volume fraction y, water volume fraction x, fuel rail temperature T, & fuel rail pressure p: $\alpha = f^*(y,x,T,p)$, $f = g^*(y,x,T,p)$, and $\delta p = h^*(y,x,T,p)$ A relationship between the above mentioned variables is given by:

$$\left\{ \begin{bmatrix} y_1 \\ \vdots \\ y_N \end{bmatrix}, \begin{bmatrix} x_1 \\ \vdots \\ x_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \left\{ \begin{bmatrix} \alpha_1 \\ \vdots \\ \alpha_N \end{bmatrix}, \begin{bmatrix} f_1 \\ \vdots \\ f_N \end{bmatrix}, \begin{bmatrix} \delta p_1 \\ \vdots \\ \delta p_N \end{bmatrix} \right\}$$

The ethanol volume fraction (y) may be determined using the inverse relationships (1*), (2*) or (3*):

$$\left\{ \begin{bmatrix} \alpha_1 \\ \vdots \\ \alpha_N \end{bmatrix}, \begin{bmatrix} f_1 \\ \vdots \\ f_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \begin{bmatrix} \hat{y}_{(\alpha,f)1} \\ \vdots \\ \hat{y}_{(\alpha,f)N} \end{bmatrix} \quad (1^*)$$

$$\left\{ \begin{bmatrix} f_1 \\ \vdots \\ f_N \end{bmatrix}, \begin{bmatrix} \delta p_1 \\ \vdots \\ \delta p_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \begin{bmatrix} \hat{y}_{(f,\delta p)1} \\ \vdots \\ \hat{y}_{(f,\delta p)N} \end{bmatrix} \quad (2^*)$$

$$\left\{ \begin{bmatrix} \alpha_1 \\ \vdots \\ \alpha_N \end{bmatrix}, \begin{bmatrix} \delta p_1 \\ \vdots \\ \delta p_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \begin{bmatrix} \hat{y}_{(\alpha,\delta p)1} \\ \vdots \\ \hat{y}_{(\alpha,\delta p)N} \end{bmatrix} \quad (3^*)$$

In certain countries, flexible fuel that is dispensed to the vehicle fuel tank may include water. Also, ethanol in fuel may adsorb water over time. At 313, water content in fuel (volume fraction) may be estimated based on the fuel rail temperature, the resonant frequency (f) of pressure pulsations, the change in fuel rail pressure (δp), and the damping coefficient (α) of pressure pulsations in the fuel rail as estimated after a fuel injection or a pump stroke. Fuel water content may be estimated as a function of the fuel rail temperature and two of the resonant frequency (f) of pressure pulsations, the change in fuel rail pressure(δp), and the damping coefficient (α) of pressure pulsations in the fuel rail. A weighted average of the estimates based on different inverse relations (1*), (2*) and (3*) may be used to improve accuracy of the estimated water content.

During conditions when fuel ethanol content is known (such as estimated), the fuel water content may be estimated as one of a first function of resonant frequency (f) and fuel rail temperature, a second function of change in fuel rail pressure (δp) in fuel and fuel rail temperature, and as a third function of damping coefficient (α) and fuel rail temperature.

In this way, in one example, the ethanol and water fractions may be estimated using mappings that are a function of two or more of the bulk modulus, speed of sound and viscosity. In another example, direct mappings relating two or more of δp, f, and α to ethanol and water fractions may be used. When using direct mappings, computation of the bulk modulus, speed of sound and viscosity as intermediate variables may not be carried.

At 314, engine operations may be adjusted based on the estimated fuel ethanol content and/or estimated fuel water content. The adjusted engine operating parameters may include adjusting an amount of injected fuel, spark timing, and/or fuel injection timing according to the detected changes in fuel composition.

For example, if the ethanol percentage increases, an octane level is higher and a spark timing may be advanced due to a higher activation energy of ethanol compared to gasoline which in turn increases the ignition period (for ethanol). Also, as ethanol content increases, the octane number increases as does cooling effect from DI injectors, therefore spark timing may be advanced from a borderline condition towards MBT timing in response to an increase in ethanol content. As another example, the amount of fuel injected on a cold start may be increased in response to an increase in ethanol content such that sufficient fuel is vaporized prior to start up the engine. As another example, the amount (mass) of injected fuel may be increased in response to increase in ethanol content due to ethanol's lower stoichiometric air-to-fuel ratio. Also, each fraction of fuel delivered via DI and PFI may be adjusted based on an increase in ethanol content.

For example, if the fuel water content increases, fuel burn rates may decrease and the ignition period may increase and a spark timing may be advanced to allow a longer ignition period. Also, as the water content in fuel increases, the fraction of gasoline and/or ethanol in fuel may decrease, therefore an amount of fuel injected may be increased by increasing injection timing and injection pulse width to maintain a desired amount of combustible (gasoline and/or ethanol) components. Further, as the fuel water content increases, during cold starts, an amount of fuel injected may be increased to maintain a desired amount of vaporized combustible components.

At 316, the routine includes determining if the fuel water content is higher than a threshold level. The threshold level may be based on a fuel water content at which a phase separation (between ethanol and water) may occur, rendering the fuel ineffective for engine operation. The threshold may be pre-calibrated to be lower than the fuel water level at which the fuel may become ineffective such that the fuel may be used up prior to the fuel degradation.

If it is determined that fuel water content is higher than the threshold water content, at 320, the operator may be notified via a dashboard indication that the fuel needs to be used up within a threshold time. The threshold time may be based on the fuel water content at which the fuel will become ineffective. In one example, the operator may refuel (add new fuel), such that the older fuel may be mixed with the newer fuel, thereby reducing the effects of the diluted fuel. If it is determined that fuel water content is lower than the threshold level, it may be inferred that the fuel may be continued to be used for engine operation. At 318, it may be indicated that the current fuel is suitable for combustion.

The above mentioned method may be used to estimate the fuel ethanol content of fuel in the fuel rail (not in fuel tank). In one example, if between refueling and ethanol content estimation, the fuel in the fuel rail is not used (such as injected to cylinders), there may be a difference in the ethanol content as estimated (based on fuel in fuel rail) relative to the ethanol content of fuel in the fuel tank. The method described in FIG. 16 may be used to estimate fuel ethanol content in the fuel tank. Therefore, since the composition of the fuel being dispensed by the port injectors might be different than the composition of the fuel being dispensed by the direct injectors, some vehicles may use both methods as described in FIG. 3 and FIG. 16 for fuel ethanol estimation.

Figure 4:
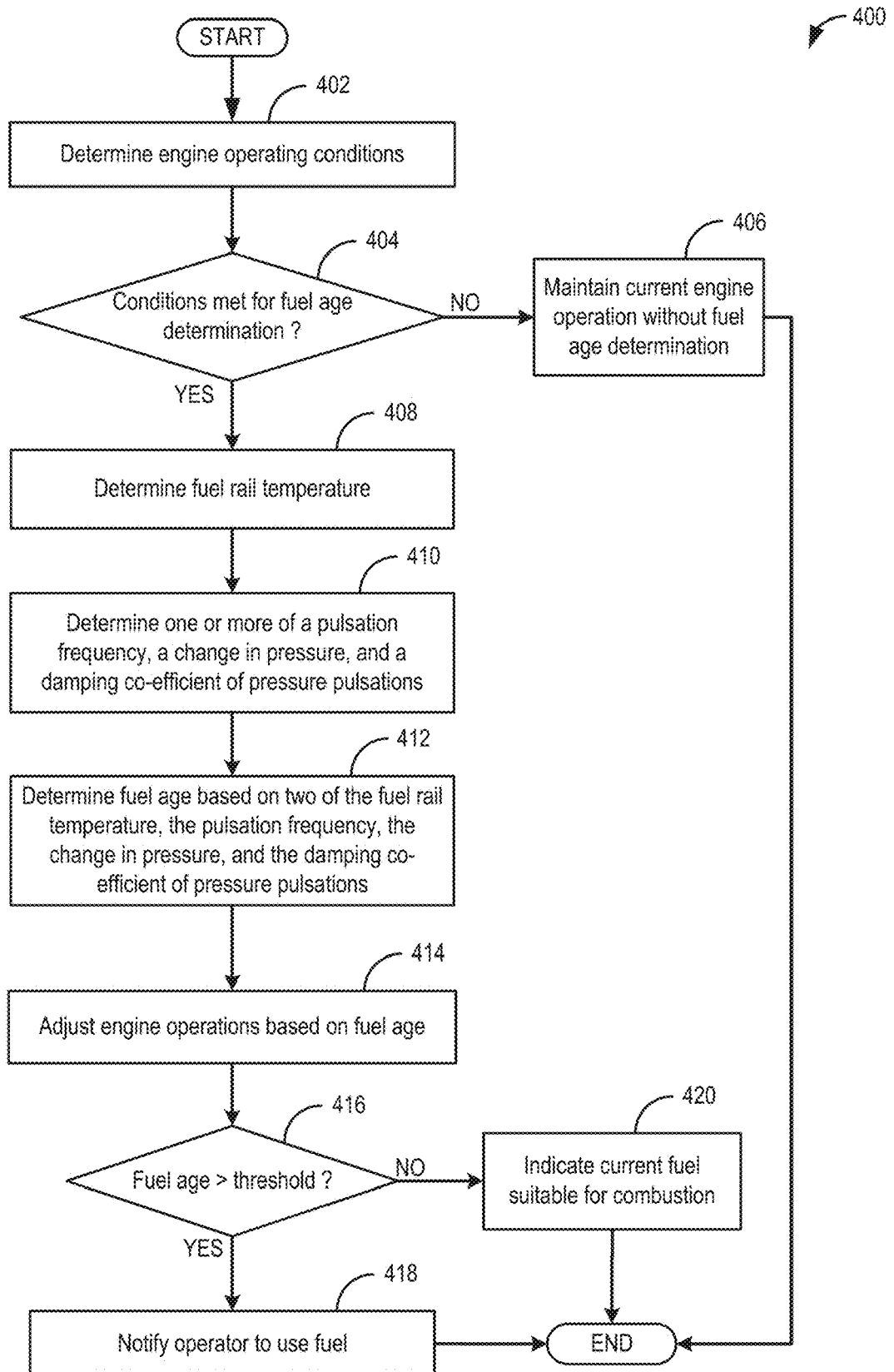
FIG. 4 shows a flow chart illustrating a first method for determining aging in gasoline.

FIG. 4 shows an example method 400 that can be implemented to estimate an age of fuel such as gasoline in the fuel tank. Fuel age is an indication of the change in fuel constituents with time due to vaporization of the fuel's lighter more volatile ends. The fuel aging process is a function of duration and conditions at which the fuel is stored in the fuel tank. At 402, current vehicle and engine operating parameters may be determined. The parameters may include vehicle speed, torque demand, engine speed, engine temperature, etc. The controller may estimate a timing of fuel injection and an amount of fuel supplied to the fuel injectors (direct injectors and/or port injectors) via the first fuel rail (such as first fuel rail 250 in FIG. 2) coupled to the direct injectors (such as direct injectors 252 in FIG. 2) and the second fuel rail (such as second fuel rail 260 in FIG. 2) coupled to the port injectors (such as port injectors 262 in FIG. 2). The controller may monitor operation of a fuel pump (such as high pressure pump 214 in FIG. 2) such as timing of a fuel pump stroke.

At 404, the routine includes determining if conditions are met for fuel age determination. Fuel age determination may be carried out in an engine using gasoline as fuel. Thus, in some examples, the fuel age determination may be carried out only in vehicles configured to operate with gasoline. In another example, fuel age estimation may be carried out in vehicles configured to operate with flexible fuel (such as containing alcohol) if the alcohol content is known (such as based on ethanol content fuel tank sensor and/or adaptation algorithms using the exhaust oxygen sensor).

The conditions may include the vehicle being propelled via engine torque with fuel being supplied to the injectors via a fuel rail (such as the first fuel rail). The conditions may also include a first threshold duration of vehicle operation with motor torque (fuel not combusting). For example, if the vehicle is operated for 7 days without engine operation, a fuel age determination may be carried out at the immediately subsequent engine start. Internal electronic control unit soak times, connect vehicles (vehicle to vehicle, infrastructure to vehicle), and/or cell phones connected to the vehicle controller may be used to access dates and determine time elapsed since previous fuel usage. The conditions may further include a second threshold duration of time elapsing since a prior fuel age estimation. For example, such estimations may be carried out periodically after every 15 days. Also, the conditions may include a third threshold duration of time during which less than a threshold quantity of fuel is consumed. If it is determined that conditions are not met for fuel age determination, at 406, current engine operation may be continued without fuel age determination. Engine operation may include supplying fuel to one or more fuel injectors via one or more fuel rails.

If it is determined that conditions are met for fuel age determination, at 408, fuel rail temperature may be estimated via a fuel rail temperature sensor (such as first fuel rail temperature sensor 232 in FIG. 2) coupled to the fuel rail. Alternatively, fuel rail temperature may be estimated using a physics-based or empirical model relating fuel rail temperature to the engine operating conditions and states.

At 410, one or more of a resonant frequency (f) of pressure pulsations, a change in fuel rail pressure ($\delta p$), and a damping coefficient ($\alpha$) of pressure pulsations in the fuel rail may be estimated after a fuel injection or a pump stroke. Fuel bulk modulus may be estimated as a function of the change in fuel rail pressure ($\delta p$) caused by a change in an amount of fuel in the fuel rail (such as at pump stroke or injection event), a speed of sound in fuel may be estimated as a function of the resonant frequency (f) of pressure pulsations in the fuel rail due to the fuel pump stroke or the fuel injection, and the fuel viscosity may be estimated as a function of the damping coefficient ($\alpha$) of pressure pulsations in the fuel rail after the fuel pump stroke or the fuel injection. Estimation of each of the resonant frequency (f) of pressure pulsations, the change in fuel rail pressure($\delta p$), and the damping coefficient ($\alpha$) of pressure pulsations in the fuel rail is discussed in details in step 310 of FIG. 3 and is not reiterated.

At 412, fuel age may be estimated based on the fuel rail temperature and at least one of the resonant frequency (f) of pressure pulsations, the change in fuel rail pressure($\delta p$), and on the damping coefficient ($\alpha$) of pressure pulsations in the fuel rail as estimated after a fuel injection or a pump stroke.

Due to fuel aging, a change in the concentration of the lighter ends (molecules with fewer Carbon atoms e.g. $C_3$ and $C_4$) and heavier ends may occur. As an example, fuel aging may cause an increase in the concentration of the heavier ends and a decrease in the concentration of the lighter ends. Each of the fuel bulk modulus, the speed of sound in fuel, and the fuel viscosity may be a function of the concentrations of the gasoline lighter and heavier ends (indicative of fuel age). Said another way, the fuel age may be estimated based on the fuel rail temperature and at least one of the estimated fuel bulk modulus, the speed of sound in fuel, and the fuel viscosity.

In this way, the fuel ethanol content may be estimated as a first function of the fuel rail temperature and two or more of the resonant frequency of pressure pulsations, the change in fuel rail pressure, and the damping coefficient of pressure pulsations, the fuel age may be estimated as a second function of the fuel rail temperature and one or more of the resonant frequency of pressure pulsations, the change in fuel rail pressure, and the damping coefficient of pressure pulsations, and the fuel water content may be estimated as a third function of the fuel rail temperature and two or more of the resonant frequency of pressure pulsations, the change in fuel rail pressure, and the damping coefficient of pressure pulsations. While computing the first function and the third function, it may be assumes that an effect of fuel aging is not significant and while computing the second function, it may be assumed that fuel ethanol content and fuel water content is either known or not significant.

At 414, engine operations may be adjusted based on the estimated fuel age. The adjusted engine operating parameters may include amount of fuel injected, spark timing, and fuel injection timing, according to the detected changes in fuel composition. For example, an aged fuel may have a larger concentration of gasoline's heavier, less volatile ends and as a result, a larger amount of fuel may be injected during a cold start. As an example, fuel injection timing and injection pulse width may be adjusted based on fuel age and/or due to different vaporization rates of the constituents of the aged fuel. The fuel injection timing and injection pulse width may be increased with an increase in fuel age. As another example, spark timing may be advanced to MBT to account for changes in the ignition period due to fuel aging.

At 416, the routine includes determining if the fuel age is higher than a threshold age. The threshold age may be based on the increased concentration of the heavier ends at which the fuel may be ineffective. The threshold may be pre-calibrated to be lower than the fuel age at which the fuel may become ineffective such that the aging fuel may be used up prior to the fuel degradation.

If it is determined that fuel age is higher than the threshold age, at 418, the operator may be notified via a dashboard indication that the fuel needs to be used up within a threshold time. The threshold time may be based on the fuel age at which the fuel will become ineffective. In one example, on a hybrid vehicle, the controller may increase the engine contribution to the total demanded power to consume the remaining fuel before it becomes ineffective. In another example, the operator may also refuel (add new fuel), such that the older (aged) fuel may be diluted, thereby reducing the effects of aged fuel. If it is determined that fuel age is lower than the threshold age, it may be inferred that the fuel may be continued to be used for engine operation. At 420, it may be indicated that the current fuel is suitable for combustion.

The above mentioned method may be used to estimate the fuel age of fuel in the fuel rail (not in fuel tank). In one example, if the vehicle is not operated via engine torque (consuming fuel) for a prolonged duration, there may be a difference in the fuel age as estimated (based on fuel in fuel rail) relative to the age of fuel in the fuel tank. The method described in FIG. 17 may be used to estimate fuel age in the fuel tank. Therefore, since the fuel age of the fuel being dispensed by the port injectors might be different than the age of the fuel being dispensed by the direct injectors, some vehicles may use both methods as described in FIG. 4 and FIG. 17 for fuel age estimation.

In this way, during a first condition, a fuel rail temperature may be estimated, volume fractions of ethanol and water in fuel contained in a fuel tank may be estimated based on an estimated fuel rail temperature and two of an estimated fuel bulk modulus, an estimated fuel viscosity, and a speed of sound in fuel, engine operation may be adjusted based on the estimated volume fraction of ethanol, and during a second condition, the fuel rail temperature may be estimated, an age of the fuel contained in the fuel tank may be estimated based on the estimated fuel rail temperature and one of the estimated fuel bulk modulus, the estimated fuel viscosity, and the speed of sound in fuel, and engine operation may be adjusted based on the age of the fuel. The first condition may include completion of a refueling event, the fuel being a flexible fuel and the second condition may include completion of a threshold distance of travel and/or duration of travel since an immediately previous fuel age estimation, the fuel being gasoline.

Figure 5:
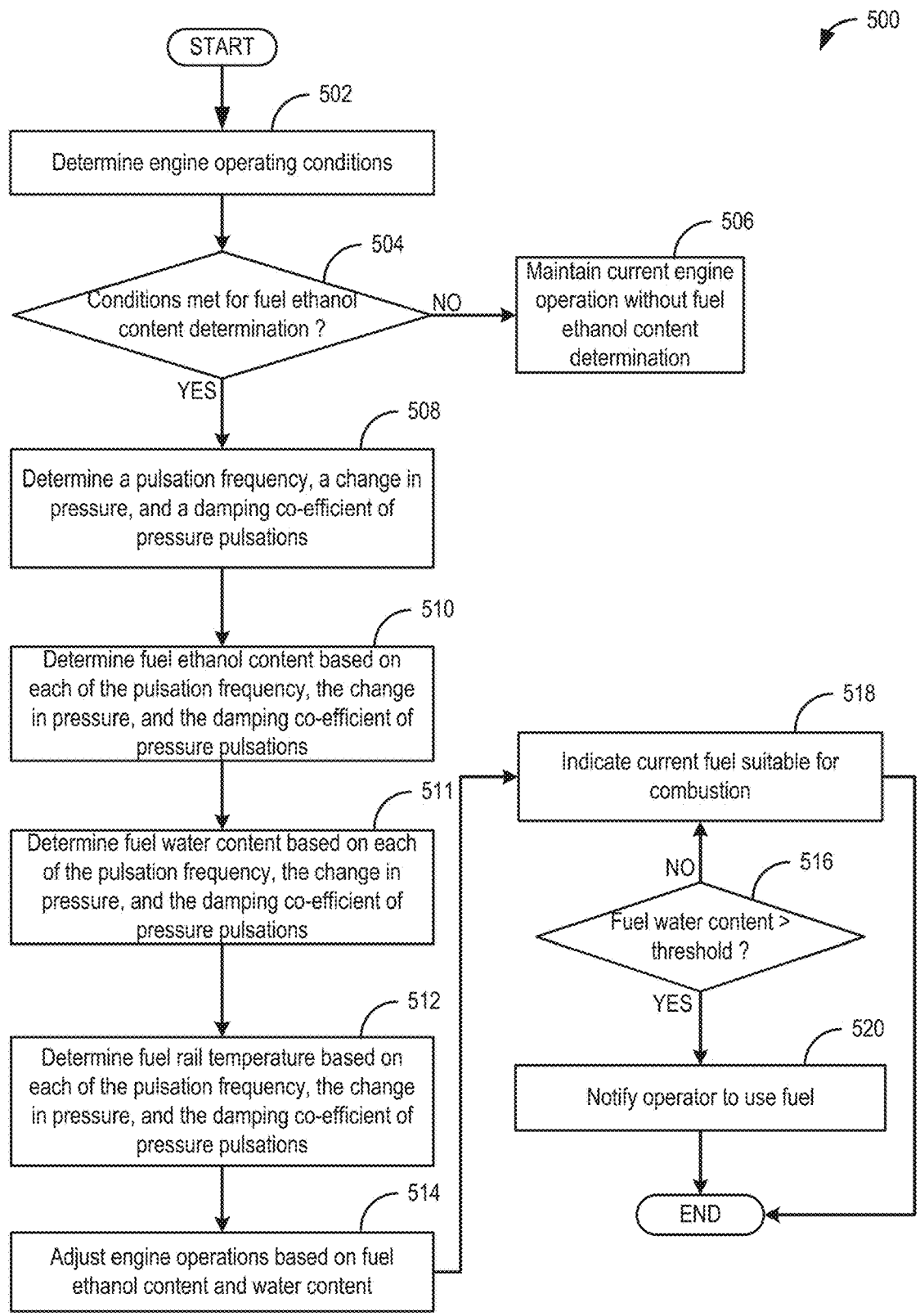
FIG. 5 shows a flow chart illustrating a second method for determining ethanol content in fuel.

FIG. 5 shows an example method 500 that can be implemented to estimate a volume fraction of ethanol in fuel and a fuel rail temperature. Unlike the method for fuel ethanol content estimation described in FIG. 3, in this method, fuel rail temperature is not used as an input for estimating the fuel ethanol content. At 502, current vehicle and engine operating parameters may be determined. The determined parameters are elaborated in step 302 in FIG. 3 and not reiterated.

At 504, the routine includes determining if conditions are met for fuel ethanol content determination. The conditions for ethanol volume fraction are elaborated in step 304 in FIG. 3 and not reiterated. If it is determined that conditions are not met for fuel ethanol content determination, at 506, current engine operation may be continued without fuel ethanol content determination. Engine operation may include supplying fuel to one or more fuel injectors via one or more fuel rails.

If it is determined that conditions are met for fuel ethanol content determination, at 508, each of a resonant frequency (f) of pressure pulsations, a change in fuel rail pressure($\delta p$), and a damping coefficient ($\alpha$) of pressure pulsations in the fuel rail may be estimated after a fuel injection or a pump stroke. Estimation of each of the resonant frequency (f) of pressure pulsations, the change in fuel rail pressure($\delta p$), and the damping coefficient ($\alpha$) of pressure pulsations in the fuel rail is discussed in details in step 310 of FIG. 3 and is not reiterated. Fuel bulk modulus may be estimated as a function of the change in fuel rail pressure ($\delta p$) caused by a change in an amount of fuel in the fuel rail (such as at pump stroke or injection event), a speed of sound in fuel may be estimated as a function of the resonant frequency (f) of pressure pulsations in the fuel rail due to the fuel pump stroke or the fuel injection, and the fuel viscosity may be estimated as a function of the damping coefficient ($\alpha$) of pressure pulsations in the fuel rail after the fuel pump stroke or the fuel injection.

At 510, fuel ethanol content (volume fraction) may be estimated based on the resonant frequency (f) of pressure pulsations, the change in fuel rail pressure($\delta p$), and the damping coefficient ($\alpha$) of pressure pulsations in the fuel rail as estimated after a fuel injection or a pump stroke. During conditions when fuel water content is not known, the fuel ethanol content may be estimated as a function of each of the resonant frequency (f) of pressure pulsations, the change in fuel rail pressure($\delta p$), and the damping coefficient ($\alpha$) of pressure pulsations in the fuel rail. Said another way, the fuel ethanol content may be estimated based on each of the estimated fuel bulk modulus, the speed of sound in fuel, and the fuel viscosity.

During conditions when fuel water content is known (or insignificant) fuel ethanol content may be estimated as a function of two of the resonant frequency (f) of pressure pulsations, the change in fuel rail pressure ($\delta p$), and the damping coefficient ($\alpha$) of pressure pulsations in the fuel rail. Fuel ethanol content may be estimated directly based on two or more of the damping coefficient $\alpha$ of pressure pulsations, fuel rail pressure pulsation frequency f, change in fuel rail pressure during a pump stroke $\delta p$, and fuel rail pressure p. As an example, damping coefficient $\alpha$, fuel rail pressure pulsation frequency f, and change in fuel rail pressure during a pump stroke $\delta p$ are a functions of ethanol volume fraction y, fuel rail temperature T, & fuel rail pressure p: $\alpha = f(y,T,p)$, $f = g(y,T,p)$, and $\delta p = h(y,T,p)$ A relationship between the above mentioned variables is given by:

$$\left\{ \begin{bmatrix} y_1 \\ \vdots \\ y_N \end{bmatrix}, \begin{bmatrix} T_1 \\ \vdots \\ T_N \end{bmatrix}, \begin{bmatrix} p_1 \\ \vdots \\ p_N \end{bmatrix} \right\} \rightarrow \left\{ \begin{bmatrix} \alpha_1 \\ \vdots \\ \alpha_N \end{bmatrix}, \begin{bmatrix} f_1 \\ \vdots \\ f_N \end{bmatrix}, \begin{bmatrix} \delta p_1 \\ \vdots \\ \delta p_N \end{bmatrix} \right\}$$

where 1, 2, . . . N are the number of measurements (data points) of each of the variables.

Inverse mapping l such that $\hat{y}_{\alpha,f} = l(\alpha, f, p)$ may be used to estimate the ethanol volume fraction without the knowledge of fuel rail temperature. l may be determined from a fit (plot) or a look-up table.

In this way, the ethanol volume fraction (y) may be determined using the relationship (4):

$$\left\{ \begin{bmatrix} \alpha_1 \\ \vdots \\ \alpha_N \end{bmatrix}, \begin{bmatrix} f_1 \\ \vdots \\ f_N \end{bmatrix}, \begin{bmatrix} p_1 \\ \vdots \\ p_N \end{bmatrix} \right\} \rightarrow \begin{bmatrix} \hat{y}_1 \\ \vdots \\ \hat{y}_N \end{bmatrix} \quad (4)$$

If dependence on fuel rail pressure (p) is negligible (such as less than 2%), fuel rail pressure (p) may be dropped from the estimation and the ethanol volume fraction may be estimated as a function of damping coefficient ($\alpha$) and fuel rail pressure pulsation frequency (f). Other alternative inverse mappings: $\hat{y}_{\alpha,\delta p}$=l*($\alpha,\delta p$, p) or $\hat{y}_{\delta p,f}$=l**($\delta p$, f,p) may be used. If dependence on fuel rail pressure (p) is negligible, fuel rail pressure (p) may also be dropped from the alternative inverse mappings.

If fuel water content is significant and unknown, the damping coefficient $\alpha$, fuel rail pressure pulsation frequency f, and change in fuel rail pressure during a pump stroke $\delta p$ are a functions of ethanol volume fraction y, water volume fraction x fuel rail temperature T, & fuel rail pressure p: $\alpha$= $f$*(y,x,T,p), f=$g$*(y,x,T,p), and $\delta p$=$h$*(y,x,T,p). In this way, ethanol content is estimated using the inverse mapping $\hat{y}$=l***($\alpha$, f, $\delta p$, p).

In certain countries, flexible fuel that is dispensed to the vehicle fuel tank may include water. Also, ethanol in fuel may adsorb water over time. At 511, water content in fuel (volume fraction) may be estimated based on each of the resonant frequency (f) of pressure pulsations, the change in fuel rail pressure ($\delta p$), and on the damping coefficient ($\alpha$) of pressure pulsations in the fuel rail as estimated after a fuel injection or a pump stroke.

At 512, fuel rail temperature may be estimated based on each of the resonant frequency (f) of pressure pulsations, the change in fuel rail pressure ($\delta p$), and the damping coefficient ($\alpha$) of pressure pulsations in the fuel rail. Fuel rail temperature (T) may be estimated directly based on two or more of the damping coefficient ($\alpha$) of pressure pulsations, fuel rail pressure pulsation frequency (f), change in fuel rail pressure during a pump stroke ($\delta p$), and fuel rail pressure (p). In one example, fuel water content is insignificant and fuel rail temperature (T) may be determined using the (inverse mapping) relationship (5):

$$\left\{ \begin{bmatrix} \alpha_1 \\ \vdots \\ \alpha_N \end{bmatrix}, \begin{bmatrix} f_1 \\ \vdots \\ f_N \end{bmatrix}, \begin{bmatrix} p_1 \\ \vdots \\ p_N \end{bmatrix} \right\} \rightarrow \begin{bmatrix} \hat{T}_1 \\ \vdots \\ \hat{T}_N \end{bmatrix} \quad (5)$$

If dependence on fuel rail pressure (p) is negligible (such as less than 2%), fuel rail pressure (p) may be dropped from the estimation and the fuel rail temperature may be estimated as a function of damping coefficient ($\alpha$) and fuel rail pressure pulsation frequency (f). In another example, fuel water content is significant and unknown, and fuel rail temperature (T) may be determined using the (inverse mapping) relationship (5*):

$$\left\{ \begin{bmatrix} \alpha_1 \\ \vdots \\ \alpha_N \end{bmatrix}, \begin{bmatrix} f_1 \\ \vdots \\ f_N \end{bmatrix}, \begin{bmatrix} \delta p_1 \\ \vdots \\ \delta p_N \end{bmatrix}, \begin{bmatrix} p_1 \\ \vdots \\ p_N \end{bmatrix} \right\} \rightarrow \begin{bmatrix} \hat{T}_1 \\ \vdots \\ \hat{T}_N \end{bmatrix} \quad (5^*)$$

Fueling may be adjusted based on the estimated fuel rail temperature. Since fuel volume is a function of pressure and temperature, injector pulse width must be modified based on fuel rail temperature to inject a target amount of fuel.

At 514, engine operations may be adjusted based on the estimated fuel ethanol and water content. Example adjustments are elaborated in step 314 in FIG. 3 and not reiterated. In this way, engine operation may be adjusted based on an estimated fuel ethanol content, the fuel ethanol content estimated based on two or more of fuel bulk modulus, fuel viscosity, and speed of sound in fuel.

At 516, the routine includes determining if the fuel water content is higher than a threshold level. The threshold level may be based on a fuel water content at which a phase separation (between ethanol and water) may occur, rendering the fuel ineffective for engine operation. The threshold may be pre-calibrated to be lower than the fuel water level at which the fuel may become ineffective such that the fuel may be used up prior to the fuel degradation.

If it is determined that fuel water content is higher than the threshold water content, at 520, the operator may be notified via a dashboard indication that the fuel needs to be used up within a threshold time. The threshold time may be based on the fuel water content at which the fuel will become ineffective. In one example, the operator may refuel (add new fuel), such that the older fuel may be mixed with the newer fuel, thereby reducing the effects of the diluted fuel. If it is determined that fuel water content is lower than the threshold level, it may be inferred that the fuel may be continued to be used for engine operation. At 518, it may be indicated that the current fuel is suitable for combustion.

Figure 6:
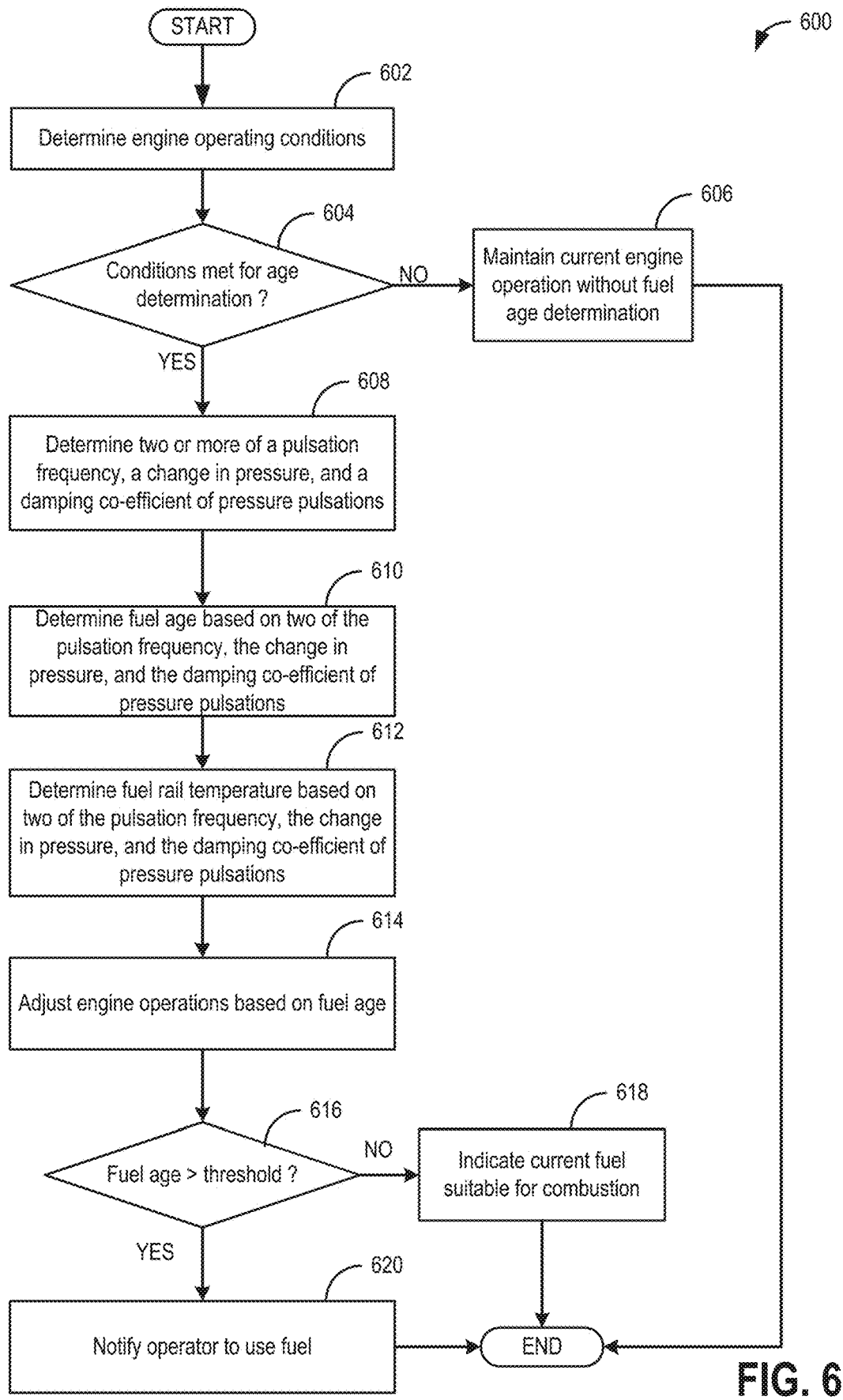
FIG. 6 shows a flow chart illustrating a second method for determining aging in gasoline.

FIG. 6 shows an example method 600 that can be implemented to estimate an age of fuel in the fuel tank and a fuel rail temperature. As previously described, fuel aging may cause an increase in the concentration of the heavier ends and a decrease in the concentration of the lighter ends. Each of the fuel bulk modulus, the speed of sound in fuel, and the fuel viscosity may be a function of the concentrations of the gasoline lighter and heavier ends (indicative of fuel age). Unlike the method for fuel age estimation described in FIG. 4, in this method, fuel rail temperature is not used as an input for estimating fuel age. At 602, current vehicle and engine operating parameters may be determined. The parameters are elaborated in step 402 in FIG. 4 and not reiterated.

At 604, the routine includes determining if conditions are met for fuel age determination. The conditions are elaborated in step 404 in FIG. 4 and not reiterated. If it is determined that conditions are not met for fuel age determination, at 606, current engine operation may be continued without fuel age determination. Engine operation may include supplying fuel to one or more fuel injectors via one or more fuel rails.

If it is determined that conditions are met for fuel age determination, at 608, two or more of a resonant frequency (f) of pressure pulsations, a change in fuel rail pressure ($\delta p$), and a damping coefficient ($\alpha$) of pressure pulsations in the fuel rail may be estimated after a fuel injection or a pump stroke. Estimation of each of the resonant frequency (f) of pressure pulsations, the change in fuel rail pressure ($\delta p$), and the damping coefficient ($\alpha$) of pressure pulsations in the fuel rail is discussed in details in step 310 of FIG. 3 and is not reiterated. Fuel bulk modulus may be estimated as a function of the change in fuel rail pressure ($\delta p$) caused by a change in an amount of fuel in the fuel rail (such as at pump stroke or injection event), a speed of sound in fuel may be estimated as a function of the resonant frequency (f) of pressure pulsations in the fuel rail due to the fuel pump stroke or the fuel injection, and the fuel viscosity may be estimated as a function of the damping coefficient ($\alpha$) of pressure pulsations in the fuel rail after the fuel pump stroke or the fuel injection.

At 610, fuel age may be estimated based on two or more of the resonant frequency (f) of pressure pulsations, the change in fuel rail pressure ($\delta p$), and the damping coefficient ($\alpha$) of pressure pulsations in the fuel rail. Fuel age, indicative of the concentrations of gasoline's lighter and heavier ends may be estimated as one of a function of resonant frequency (f) and damping coefficient ($\alpha$), a second function of change in fuel rail pressure ($\delta p$) in fuel and damping coefficient ($\alpha$), and as a third function of damping coefficient ($\alpha$) and resonant frequency (f). A weighted average of the estimates from two or three of aforementioned functions may be used to improve accuracy. Said another way, the fuel age may be estimated based on at least two of the estimated fuel bulk modulus, the speed of sound in fuel, and the fuel viscosity.

At 612, fuel rail temperature may be estimated as a function of at least two of the resonant frequency (f) of pressure pulsations, the change in fuel rail pressure ($\delta p$), and the damping coefficient ($\alpha$) of pressure pulsations in the fuel rail.

At 614, engine operations may be adjusted based on the estimated fuel age. Example adjustments are elaborated in step 414 in FIG. 4 and not reiterated. At 616, the routine includes determining if the fuel age is higher than a threshold age. The threshold age may be based on the increased the concentration of the heavier ends at which the fuel may be ineffective. The threshold may be pre-calibrated to be lower than the fuel age at which the fuel may become ineffective such that the aging fuel may be used up prior to the fuel degradation. If it is determined that fuel age is higher than the threshold age, at 620, the operator may be notified via a dashboard indication that the fuel needs to be used up within a threshold time. In one example, on a hybrid vehicle, the controller may increase the engine contribution to the total demanded power to consume the remaining fuel before it becomes ineffective. In another example, the operator may refuel (add new fuel), such that the older (aged) fuel may be diluted, thereby reducing the effects of aged fuel. At 618, it may be indicated that the current fuel is suitable for combustion and fuel change notification may not be provided.

In this way, during a first condition, a volume fractions of ethanol and water in fuel contained in a fuel tank may be estimated based on (at least) two of an estimated fuel bulk modulus, an estimated fuel viscosity, and a speed of sound in fuel, and engine operation may be adjusted based on the estimated volume fraction of ethanol, and during a second condition, an age of the fuel contained in the fuel tank may be estimated based on (at least) two of the estimated fuel bulk modulus, the estimated fuel viscosity, and the speed of sound in fuel, and engine operation may be adjusted based on the age of the fuel, and during each of the first condition and the second condition, a fuel rail temperature may be estimated based on (at least) two of the estimated fuel bulk modulus, the estimated fuel viscosity, and the speed of sound in fuel. The first condition may include completion of a refueling event, the fuel being a flexible fuel and the second condition may include completion of a threshold distance of travel and/or duration of travel since an immediately previous fuel age estimation, the fuel being gasoline.

Figure 16:
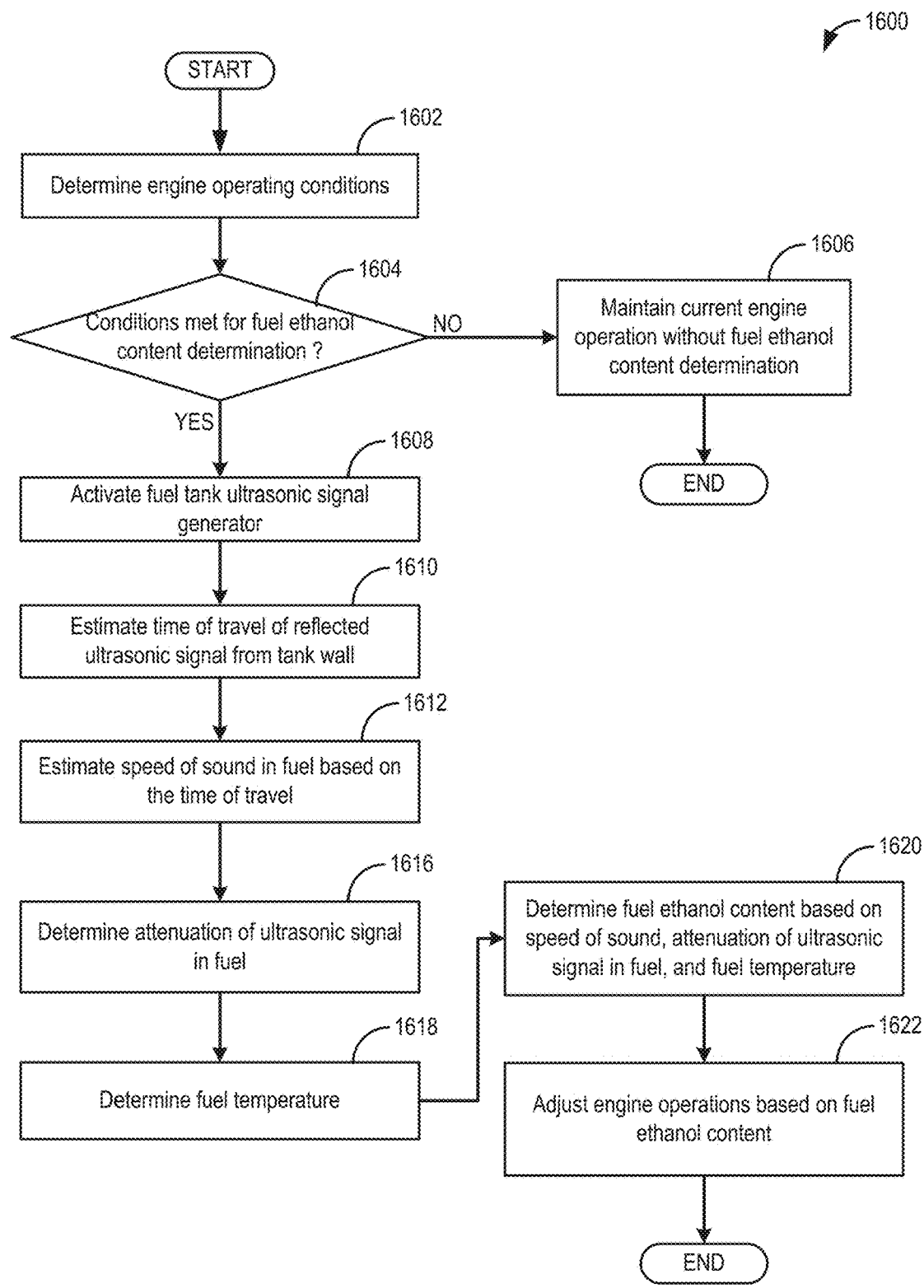
FIG. 16 shows a flow chart illustrating a third method for determining ethanol content in fuel.

FIG. 16 shows an example method 1600 that can be implemented to estimate a volume fraction of ethanol in a flexible-fuel containing ethanol. In contrast to the method for fuel ethanol content estimation, as described in FIG. 3, this method may be used to determine ethanol content of fuel in the fuel tank instead of the fuel rail. Since this method uses sensors housed in the fuel tank for ethanol content estimation, this method may be used in systems that do not have direct injectors coupled to a fuel rail and/or may be carried out during engine operation when fuel is being dispensed by port injectors.

At 1602, current vehicle and engine operating parameters may be determined. The parameters may include vehicle speed, torque demand, engine speed, engine temperature etc. The controller may estimate an amount of fuel supplied to the fuel injectors (such as the port injectors 262 in FIG. 1) from a fuel tank.

At 1604, the routine includes determining if conditions are met for fuel ethanol content determination. The conditions may include a refueling event. During refueling, fuel remaining in the fuel tank may mix with the fuel that is being dispensed resulting in a fuel blend of existing and new fuel. The ethanol content of the fuel blend may be estimated within a threshold duration (or a threshold distance of travel) after the refueling event. For example, such estimations may be carried out within 1 day of refueling or within 10 miles of travel after refueling. The conditions may further include a threshold duration of time elapsing since a prior fuel ethanol content estimation. For example, such estimations may be carried out periodically after every 15 days.

If it is determined that conditions are not met for fuel ethanol content determination, at 606, current engine operation may be continued without fuel ethanol content determination. Engine operation may include supplying fuel to one or more fuel injectors from the fuel tank. If it is determined that the conditions are met for fuel ethanol content determination, at 1608, a fuel tank ultrasonic signal generator (such as ultrasonic signal generator 240 in FIG. 2) coupled inside of a fuel tank (to a first fuel tank wall) may be activated. The ultrasonic signal generator may generate an ultrasonic signal which may travel from the first wall of the fuel tank (at which the generator is positioned) to an opposite, second, wall of the fuel tank through the fuel. The ultrasonic signal generator may be reflected from the second wall of the tank and may return to the first wall. The reflected ultrasonic signal may be received at an ultrasonic sensor (such as ultrasonic sensor 241 in FIG. 2) coupled to the first wall, adjacent to the ultrasonic signal generator.

At 1610, a time of travel of the reflected ultrasonic signal from the second fuel tank wall may be estimated. As an example, upon first generation of an ultrasonic signal by the generator located at the first wall, a timer may be set, and upon return of the reflected ultrasonic signal (from the second wall), as detected by the ultrasonic sensor coupled proximal to the generator, the timer may be stopped. The duration of time elapsed between the start and stop of the timer may be the time of travel of the ultrasonic signal to and from the second wall.

At 1612, a speed of sound in fuel may be estimated based on the estimated time of travel. The distance between the first wall and the second wall may be retrieved from controller memory. The speed of sound in fuel may be estimated as a function of the distance between the first wall and the second wall and the estimated time of travel of the ultrasonic signal.

At 1616, an attenuation of ultrasonic signal in fuel may be estimated. As the ultrasonic signal travels through fuel, between the first wall and the second wall, the signal may be attenuated. Said another way, the amplitude of the ultrasonic signal that is generated at the first wall may be higher than the amplitude of the ultrasonic signal received at the first wall after travelling back and forth through the fuel. The ultrasonic sensor may estimate a difference in amplitude between the generated ultrasonic signal and the reflected ultrasonic signal to infer the attenuation co-efficient of the ultrasonic signal. The attenuation coefficient may also be dependent on a material of the fuel tank. The level of attenuation of the ultrasonic signal in fuel may vary based on a material of the fuel tank wall at which the signal is reflected. As an example, certain materials (such as metals) may adsorb a part of the signal when the signal is reflected from the wall. Also, the level of attenuation may be based on a thickness of the wall from which the signal is being reflected. The controller may use a look-up table calibrated based on the material and thickness of the fuel tank wall to determine the attenuation co-efficient of the ultrasonic signal in fuel with one or more of the difference in signal amplitude, the distance between the first wall and the second wall, and a time of travel of ultrasonic signal to and from the second wall as inputs, and the attenuation co-efficient as the output. The attenuation co-efficient may be a function of fuel's viscosity and may be a based on the fuel ethanol content.

At 1618, temperature of fuel in the fuel tank may be estimated based on inputs from a fuel temperature sensor (such as temperature sensor 243 in FIG. 2) coupled to the fuel tank. At 1620, fuel ethanol content (volume fraction) may be estimated as a function of the speed of sound in fuel, temperature of fuel, and attenuation coefficient in fuel. Further, the fuel ethanol content may also be based on fuel pressure, however, fuel pressure may remain substantially constant during the measurement and among different measurements.

At 1622, engine operations may be adjusted based on the estimated fuel ethanol content. The adjusted engine operating parameters may include amount of injected fuel, spark timing, and/or fuel injection timing, according to the current fuel ethanol content. For example, if the ethanol percentage increases, a spark timing may be advanced due to a higher activation energy of ethanol compared to gasoline and thus a longer ignition period for ethanol. As another example, the amount of fuel injected on a cold start may be increased in response to an increase in ethanol content such that sufficient fuel is vaporized to start up the engine. As another example, the amount (mass) of injected fuel may be increased in response to increase in ethanol content due to ethanol's lower stoichiometric air-to-fuel ratio.

In this way, engine operation may be adjusted based on an estimated fuel ethanol content, the fuel ethanol content estimated based on each of a fuel temperature, a speed of sound in fuel, and an attenuation co-efficient of an ultrasonic signal in fuel.

Figure 17:
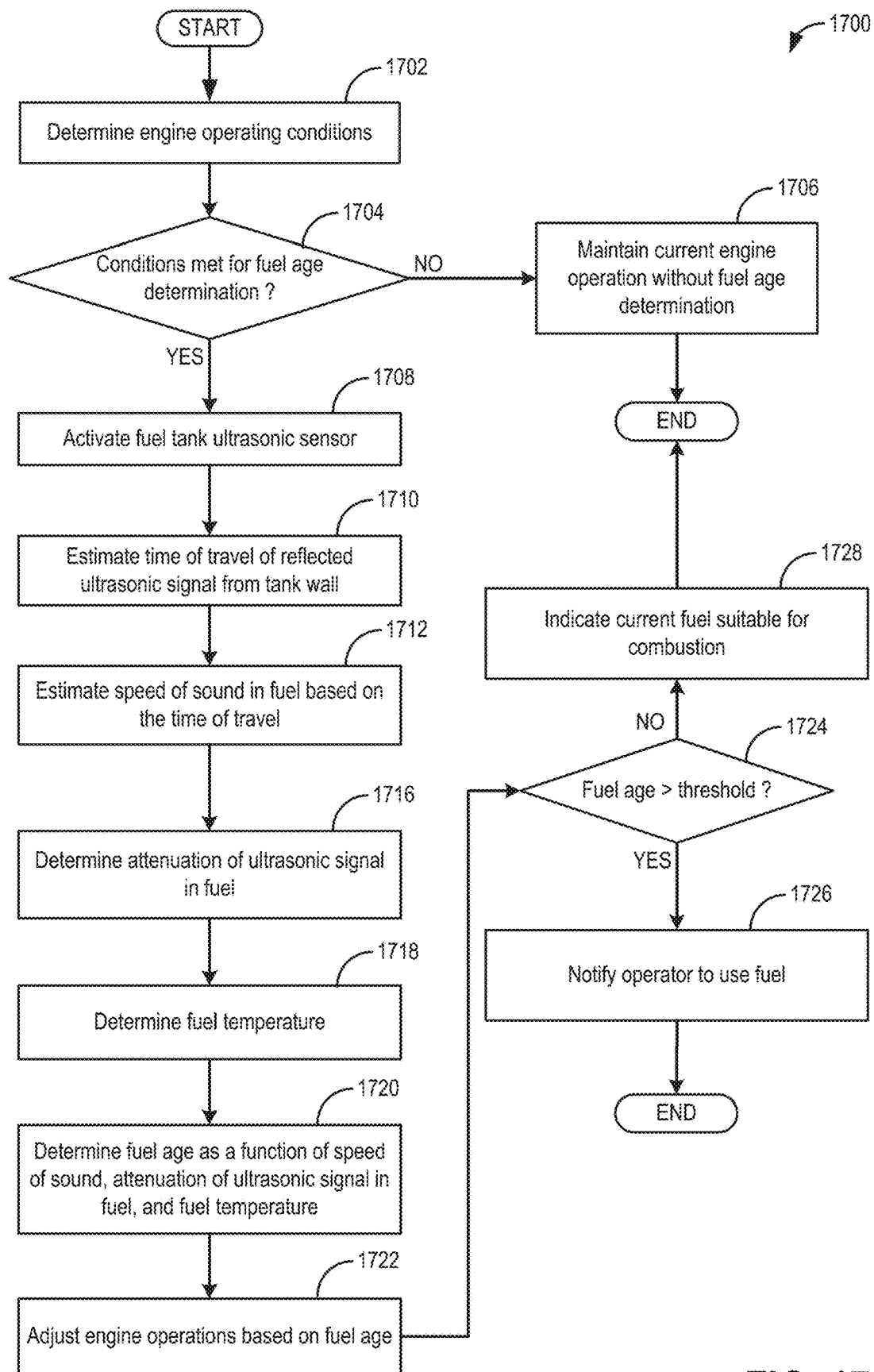
FIG. 17 shows a flow chart illustrating a third method for determining aging in fuel.

FIG. 17 shows an example method 1700 that can be implemented to estimate an age of fuel in the fuel tank. In contrast to the method for fuel age estimation, as described in FIG. 4, this method may be used to determine age of fuel in the fuel tank instead of the fuel rail. Since this method uses sensors housed in the fuel tank for fuel age estimation, this method may be used in systems that do not have direct injectors coupled to a fuel rail and/or may be carried out during engine operation when fuel is being dispensed by port injectors.

At 1702, current vehicle and engine operating parameters may be determined. The parameters may include vehicle speed, torque demand, engine speed, engine temperature etc. The controller may estimate an amount of fuel supplied to the fuel injectors (such as the port injectors 262 in FIG. 1) from a fuel tank.

At 1704, the routine includes determining if conditions are met for fuel age determination. The conditions may include, a first threshold duration of vehicle operation with motor torque (fuel not combusting). For example, if the vehicle is operated for 7 days without engine operation, a fuel age determination may be carried out at the immediately subsequent engine start. The conditions may further include a second threshold duration of time elapsing since a prior fuel age estimation. For example, such estimations may be carried out periodically after every 15 days. Also, the conditions may include a third threshold duration of time during which less than a threshold quantity of fuel is consumed. If it is determined that conditions are not met for fuel age determination, at 1706, current engine operation may be continued without fuel age determination. Engine operation may include supplying fuel to one or more fuel injectors via one or more fuel rails.

If it is determined that conditions are met for fuel age determination, at 1608, a fuel tank ultrasonic signal generator (such as ultrasonic signal generator 240 in FIG. 2) coupled inside of a fuel tank (to a first fuel tank wall) may be activated. The ultrasonic signal generator may generate an ultrasonic signal which may travel from the first wall of the fuel tank (at which the generator is positioned) to an opposite, second, wall of the fuel tank through the fuel. The ultrasonic signal generator may be reflected from the second wall of the tank and may return to the first wall. The reflected ultrasonic signal may be received at an ultrasonic sensor (such as ultrasonic sensor 241 in FIG. 2) coupled to the first wall, adjacent to the ultrasonic signal generator.

At 1710, a time of travel of the reflected ultrasonic signal from the second fuel tank wall may be estimated. As an example, upon first generation of an ultrasonic signal by the generator located at the first wall, a timer may be set, and upon return of the reflected ultrasonic signal (from the second wall), as detected by the ultrasonic sensor coupled proximal to the generator, the timer may be stopped. The duration of time elapsed between the start and stop of the timer may be the time of travel of the ultrasonic signal to and from the second wall.

At 1712, a speed of sound in fuel may be estimated based on the estimated time of travel. The distance between the first wall and the second wall may be retrieved from controller memory. The speed of sound in fuel may be estimated as a function of the distance between the first wall and the second wall and the estimated time of travel of the ultrasonic signal.

At 1716, attenuation of ultrasonic signal in fuel may be estimated. As the ultrasonic signal travels through fuel, between the first wall and the second wall, the signal may be attenuated. The ultrasonic sensor may estimate a difference in amplitude between the generated ultrasonic signal and the reflected ultrasonic signal to infer the attenuation co-efficient of the ultrasonic signal. The annotation constant may also be dependent on a material of the fuel tank. The level of attenuation of the ultrasonic signal in fuel may vary based on a material of the fuel tank wall at which the signal is reflected. As an example, certain materials (such as metals) may adsorb a part of the signal when the signal is reflected from the wall. Also, the level of attenuation may be based on a thickness of the wall from which the signal is being reflected. The controller may use a look-up table calibrated based on the material and thickness of the fuel tank wall to determine the attenuation co-efficient of the ultrasonic signal in fuel with one or more of the difference in signal amplitude, the distance between the first wall and the second wall, and a time of travel of ultrasonic signal to and from the second wall as inputs, and the attenuation co-efficient as the output. The attenuation co-efficient may be a function of the fuel's viscosity and may be a based on the fuel age.

At 1718, temperature of fuel in the fuel tank may be estimated based on inputs from a fuel temperature sensor (such as temperature sensor 243 in FIG. 2) coupled to the fuel tank. At 1720, fuel age, indicative of the concentrations of gasoline's lighter and heavier ends, may be estimated based on each of the estimated speed of sound in fuel, attenuation co-efficient in fuel, and fuel temperature.

At 1722, engine operations may be adjusted based on the estimated fuel age. The adjusted engine operating parameters may include amount of injected fuel, spark timing, and/or fuel injection timing according to the detected changes in fuel composition. For example, an aged fuel may have a larger concentration of gasoline's heavier, less volatile ends and as a result, a larger amount of fuel may be injected during a cold start.

At 1724, the routine includes determining if the fuel age is higher than a threshold age. The threshold age may be based on the increased the concentration of the heavier ends at which the fuel may be ineffective. The threshold may be pre-calibrated to be lower than the fuel age at which the fuel may become ineffective such that the aging fuel may be used up prior to the fuel degradation.

If it is determined that fuel age is higher than the threshold age, at 1726, the operator may be notified via a dashboard indication that the fuel needs to be used up within a threshold time. The threshold time may be based on the fuel age at which the fuel will become ineffective. In one example, on a hybrid vehicle, the controller may increase the engine contribution to the total demanded power to consume the remaining fuel before it becomes ineffective. In another example, the operator may refuel (add new fuel), such that the older (aged) fuel may be diluted, thereby reducing the effects of aged fuel. If it is determined that fuel age is lower than the threshold age, it may be inferred that the fuel may be continued to be used for engine operation. At 1728, it may be indicated that the current fuel is suitable for combustion.

In this way, an ultrasonic signal may be generated via an ultrasonic signal generator positioned on a first wall of a fuel tank, a reflected ultrasonic signal reflected from a second, opposite wall of the fuel tank may be received, via an ultrasonic sensor, a speed of sound in fuel housed in the fuel tank and an attenuation co-efficient of ultrasonic signal in the fuel may be estimated based on the generated signal and the reflected signal, a percentage of ethanol in the fuel or an age of the fuel may be estimated based on the estimated speed of sound in the fuel, the estimated attenuation co-efficient of ultrasonic signal in the fuel, and fuel temperature, and engine operation may be adjusted based on the estimated percentage of ethanol in fuel or the age of the fuel.

Figure 14:
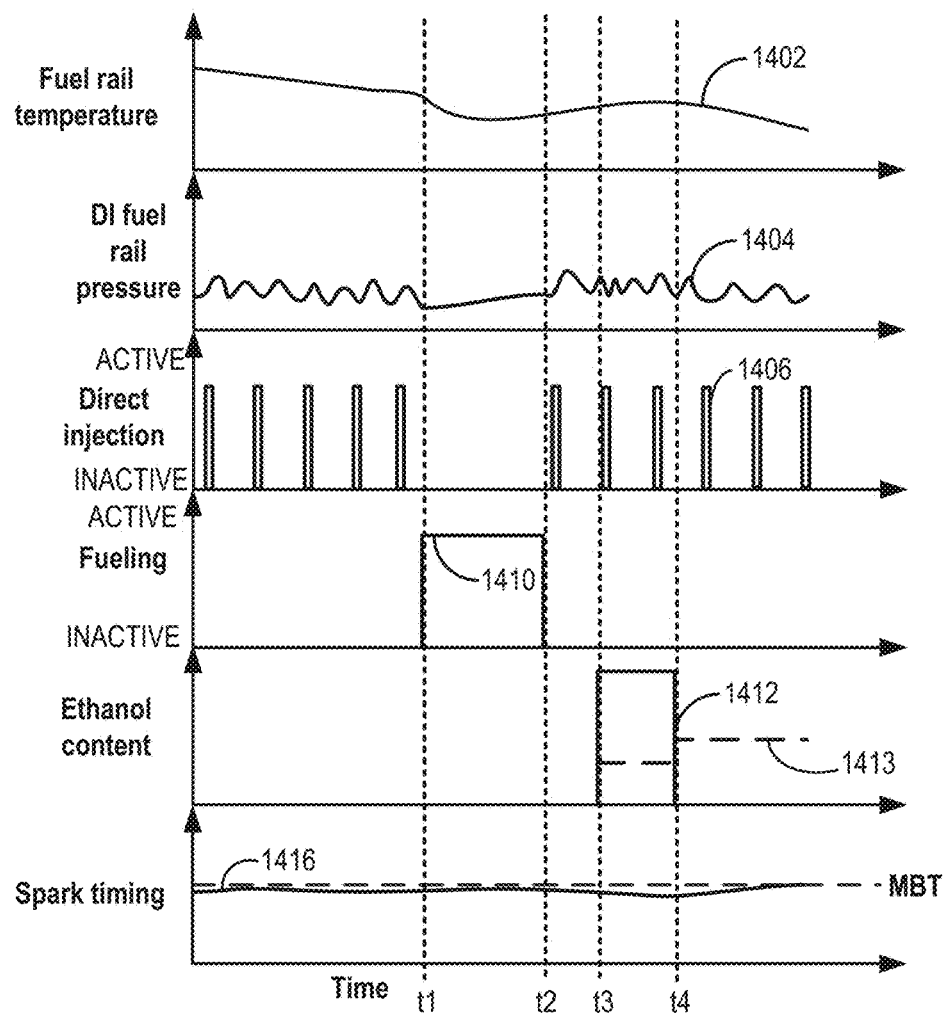
FIG. 14 shows an example determination of fuel ethanol content using fuel rail pressure.

FIG. 14 shows an example timeline 1400 illustrating determination of fuel ethanol content in an alcohol containing fuel (flex-fuel) in gasoline using fuel rail pressure. In one example, fuel ethanol content estimation may be carried out for vehicle engines such as a flex-fuel engine. The horizontal (x-axis) denotes time and the vertical markers t1-t4 identify significant times in the routine for fuel ethanol content and fuel age determination.

The first plot, line 1402, shows a variation in fuel rail temperature as estimated via a fuel rail temperature sensor (such as temperature sensor 232 in FIG. 2) coupled to the fuel rail (such as fuel rail 250 in FIG. 2). The second plot, line 1404, shows a variation in fuel rail pressure as measured via a fuel rail pressure sensor (such as pressure sensor 248 in FIG. 2) coupled to the fuel rail. The third plot, line 1406, shows fuel direct injection pulses. At each pulse, fuel is delivered from the fuel rail to the combustion chamber via the direct injectors (such as direct injectors 252 in FIG. 2). The fourth plot, line 1410, shows a refueling event when fuel is dispensed to the fuel tank, via an external nozzle, at a gas station. The fifth plot, line 1412, shows an ethanol content estimation event. The sixth plot, line 1416, shows spark timing relative to maximum brake torque (MBT) timing.

Prior to time t1, fuel is injected via direct injection and the pump is operated to transfer fuel from the fuel tank to the fuel rail for injection. The fuel rail pressure fluctuates based on fuel injection events. The spark timing is adjusted based on engine operating conditions. Fuel ethanol content is not carried out at this time. At time t1, a fueling event is initiated and fuel is dispensed into the fuel tank from an external source. Between time t1 and t2, during the fueling event, as the vehicle is not being propelled, fuel is not injected to the combustion chamber. As newly added fuel mixes with the existing fuel in the fuel tank, the ethanol content of the mixed fuel may change.

At time t2, fueling is completed and engine operation is resumed. Between time t2 and t3, fuel is pumped from the fuel tank to the fuel rail and fuel is injected to the combustion chambers via the fuel injectors. At time t3, an ethanol content estimation is initiated and a change in the fuel rail pressure during a fuel injection is recorded. The change in fuel rail pressure is a difference in fuel rail pressure before and after the fuel injection. Each of a resonant frequency of pressure pulsations in the fuel rail and a damping coefficient of pressure pulsations in the fuel rail immediately after the fuel injection are estimated. The fuel ethanol content is estimated as a function of three or more of a fuel rail temperature, the change in fuel rail pressure, resonant frequency of pressure pulsations in the fuel rail, and the damping coefficient of pressure pulsations. Fuel ethanol content estimation is completed at time t4. As seen from the dashed line 1413, after the ethanol content estimation, it is confirmed that the fuel ethanol content has increased after the fueling event (between time t1 and t2). Activation energy of ethanol is higher compared to gasoline and thus a higher ethanol content would require a longer ignition period. Therefore, in response to the increased fuel ethanol content, after time t4, the engine is operated with spark timing advanced to MBT. Due to the advanced spark timing, engine efficiency is improved.

Figure 15:
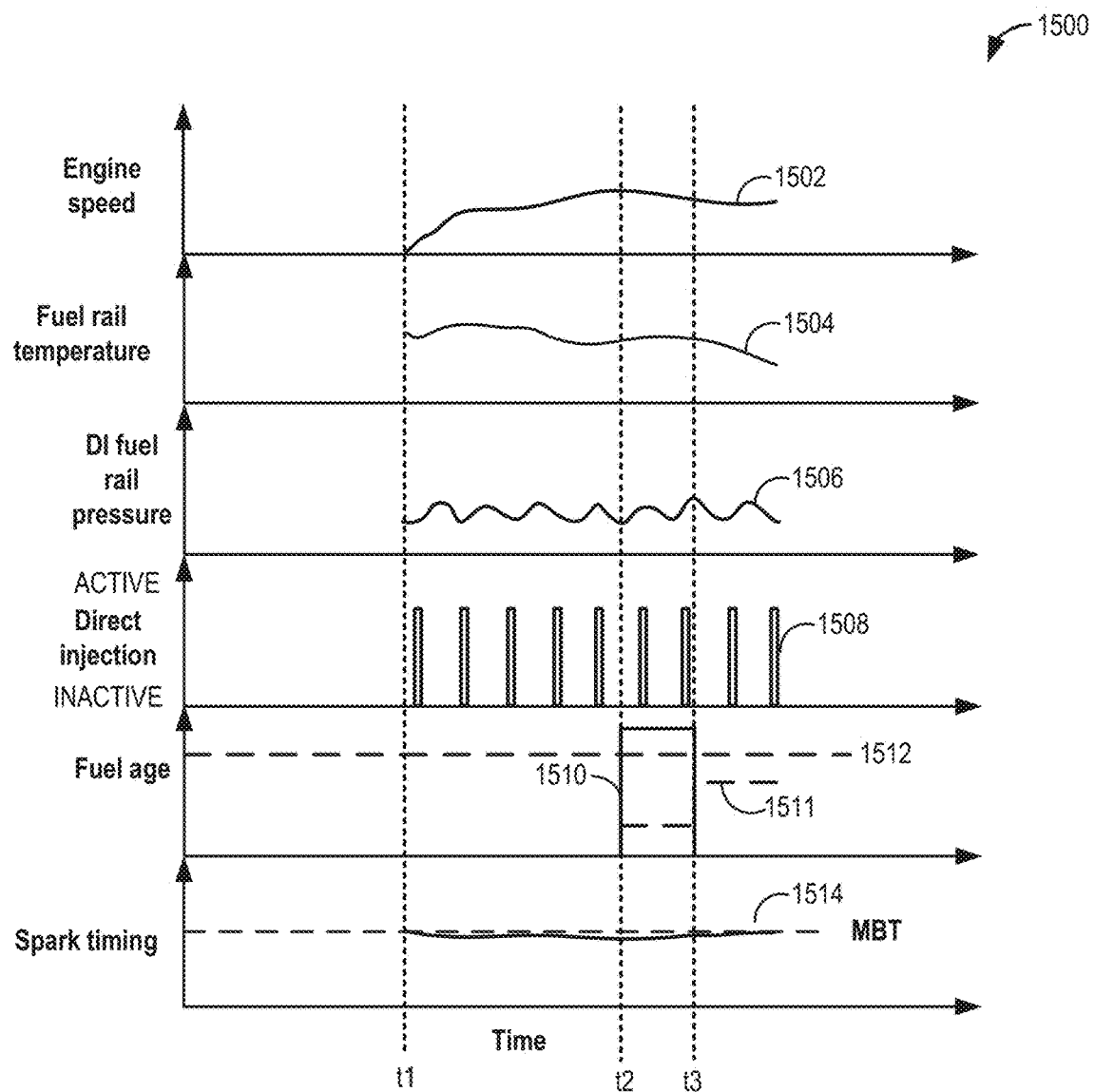
FIG. 15 shows an example determination of fuel age using fuel rail pressure.

FIG. 15 shows an example timeline 1500 illustrating determination of fuel age based on fuel rail pressure. The horizontal (x-axis) denotes time and the vertical markers t1-t3 identify significant times in the routine for fuel age determination. In one example, fuel age estimation may be carried out in vehicles using gasoline as fuel. In another example, fuel age estimation may be carried out for a flex-fuel vehicle wherein the ethanol content of the fuel is known.

The first plot, line 1502, shows a variation in engine speed as estimated via a crankshaft sensor. The second plot, line 1504, shows fuel rail temperature as estimated via a fuel rail temperature sensor (such as temperature sensor 232 in FIG. 2) coupled to the fuel rail (such as fuel rail 250 in FIG. 2). The third plot, line 1506, shows a variation in fuel rail pressure as measured via a fuel rail pressure sensor (such as pressure sensor 248 in FIG. 2) coupled to the fuel rail. The fourth plot, line 1508, shows fuel direct injection pulses. At each pulse, fuel is delivered from the fuel rail to the combustion chamber via the direct injectors (such as direct injectors 252 in FIG. 2). The fifth plot, line 1510, shows a fuel age estimation event. Dashed line 1511 shows an estimated fuel age. Dashed line 1512 shows a threshold fuel age above which the operator is notified to use up the fuel. The threshold may be pre-calibrated to be lower than the fuel age at which the fuel may become ineffective such that the aging fuel may be used up prior to the fuel degradation. The sixth plot, line 1514, shows spark timing relative to maximum brake torque (MBT) timing.

Prior to time t1, the engine is not operated as the vehicle is not propelled via engine torque. Fuel injection and spark is disabled during engine shut-down. At time t1, the engine is started from rest and fuel is injected to engine cylinders via direct injection. The fuel rail pressure fluctuates based on fuel injection events. The spark timing is adjusted based on engine operating conditions. Fuel age estimation is not carried out at this time.

At time t2, it is inferred that a threshold duration had elapsed since the previous fuel age determination. Therefore, at time t2, a fuel age estimation is initiated. The fuel age is estimated as a function of two or more of a fuel rail temperature, change in fuel rail pressure, resonant frequency of pressure pulsations in the fuel rail, and the damping coefficient of pressure pulsations. Fuel age estimation is completed at time t3. After the fuel age estimation, it is confirmed that the fuel age has increased. However, since the fuel age continues to be below the threshold age 1512, the operator is not notified. In response to the increased fuel age, after time t3, the engine is operated with spark timing advanced to MBT. Due to the advanced spark timing, engine efficiency is improved.

In this way, fuel ethanol content or fuel age may be estimated based on fuel rail pressure and then engine operation such as spark timing may be adjusted to improve fuel efficiency and engine performance.

Figure 18:
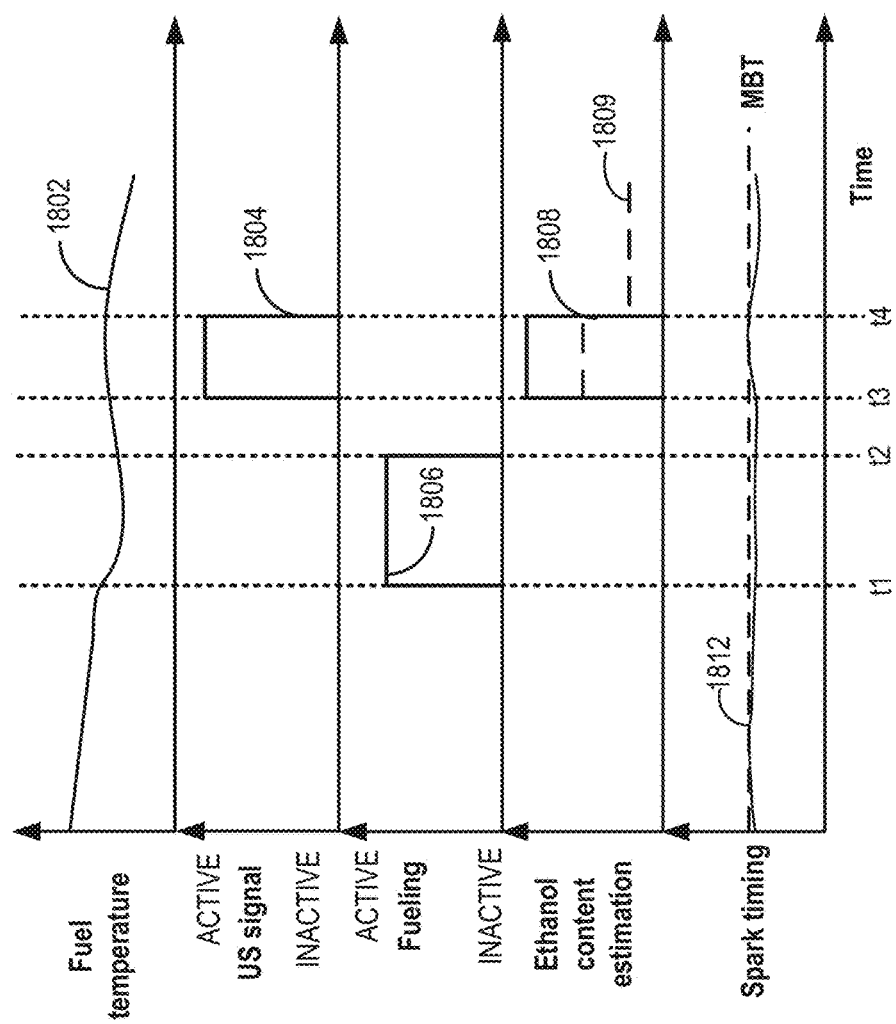
FIG. 18 shows an example determination of fuel ethanol content using an ultrasonic signal.

FIG. 18 shows an example timeline 1800 illustrating determination of fuel ethanol content based on ultrasonic signal. The horizontal (x-axis) denotes time and the vertical markers t1-t4 identify significant times in the routine for fuel ethanol content determination.

The first plot, line 1802, shows a variation in fuel temperature as estimated via a fuel temperature sensor (such as temperature sensor 243 in FIG. 2) coupled inside the fuel tank. The second plot, line 1804, shows generation of an ultrasonic signal from an ultrasonic signal generator (such as ultrasonic signal generator 240 in FIG. 2). The ultrasonic signal generator is coupled to a first wall of the fuel tank, and the generated ultrasonic signal gets reflected from a second, opposite wall of the fuel tank. The reflected ultrasonic signal is recorded by an ultrasonic signal sensor (such as ultrasonic signal sensor 241 in FIG. 2) coupled to the first wall, proximal to the ultrasonic signal generator. The third plot, line 1806, shows a fueling event when fuel is dispensed to the fuel tank, via an external nozzle, at a gas station. The fourth plot, line 1808, shows an ethanol content estimation event. Dashed line 1809 shows an estimated fuel ethanol content during and after the ethanol content estimation event. The fifth plot, line 1812, shows spark timing relative to maximum brake torque (MBT) timing.

Prior to time t1, the vehicle is propelled by engine torque and the spark timing is maintained at MBT. Fuel temperature changes are based on engine operation and fuel is not supplied to the fuel tank. Fuel ethanol content or fuel age estimation is not carried out at this time and the ultrasonic signal generator and sensor remain inactive. At time t1, a fueling event is initiated and fuel is dispensed into the fuel tank. Between time t1 and t2, during the fueling event, as the vehicle is not being propelled and the engine is not operated. As newly added fuel mixes with the existing fuel in the fuel tank, the ethanol content of the mixed fuel may change.

At time t2, fueling is completed and engine operation is resumed. Between time t2 and t3, fuel is injected to the combustion chambers via the fuel injectors. At time t3, ethanol content estimation of the fuel in the tank is initiated. In order to estimate the fuel ethanol content, the ultrasonic signal generator is activated to generate ultrasonic signal. The ultrasonic signal, upon reflection from the opposite wall of the fuel tank is detected by the ultrasonic sensor. A speed of sound in fuel is estimated based on a time of travel of the ultrasonic signal through the fuel, back and forth between a first wall of the fuel tank and a second, opposite, wall of the fuel tank, and a distance between the first wall and the second wall. An attenuation coefficient of the ultrasonic signal is estimated based on a change in amplitude of the ultrasonic signal reaching the ultrasonic signal sensor after being reflected from the second wall. The fuel ethanol content is estimated based on each of a fuel temperature, a speed of sound in the fuel, and an attenuation coefficient of ultrasonic signal in the fuel. Fuel ethanol content estimation is completed at time t4. As seen from the dashed line 1809, after the ethanol content estimation, it is confirmed that the fuel ethanol content has decreased after the fueling event (between time t1 and t2). Due to the ethanol content decreasing, between time t4 and t5, the spark timing is retarded MBT.

Figure 19:
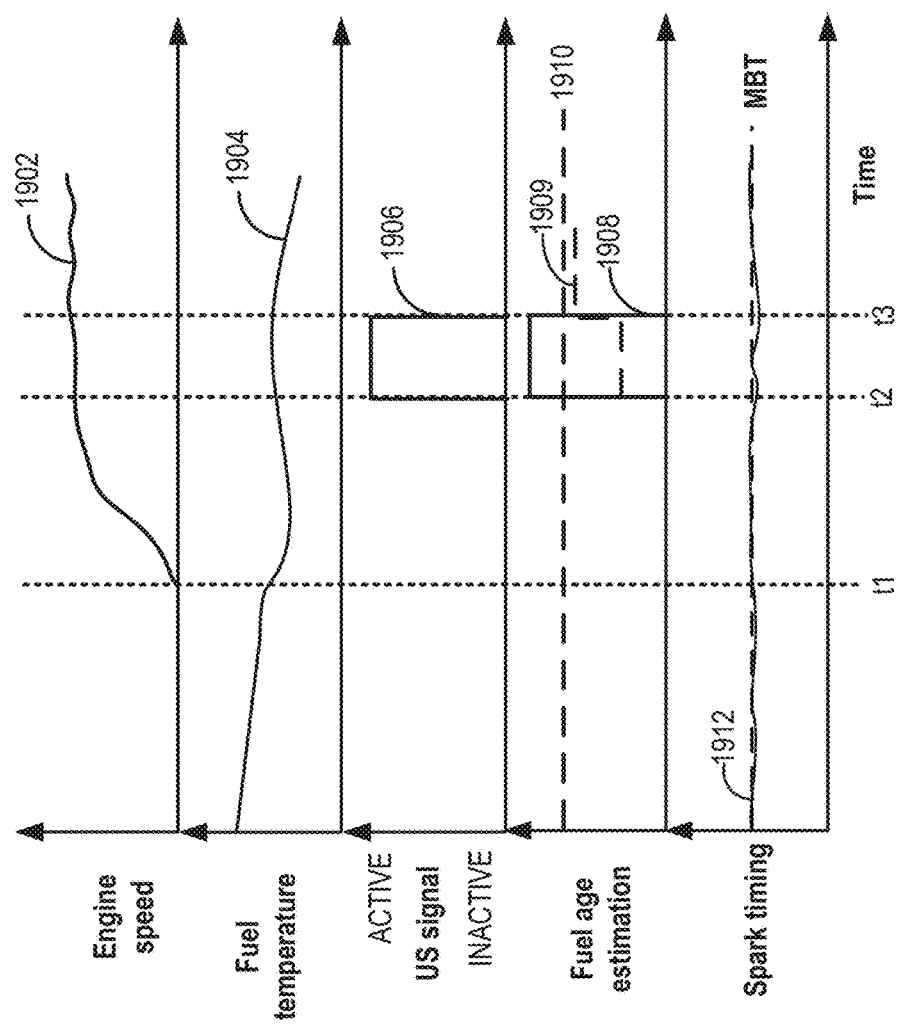
FIG. 19 shows an example determination of fuel age using an ultrasonic signal.

FIG. 19 shows an example timeline 1900 illustrating determination of fuel age based on ultrasonic signal. The horizontal (x-axis) denotes time and the vertical markers t1-t3 identify significant times in the routine for fuel age determination.

The first plot, line 1902, shows a variation in engine speed as estimated via a crankshaft sensor. The second plot, line 1904, shows a variation in fuel temperature as estimated via a fuel temperature sensor (such as temperature sensor 243 in FIG. 2) coupled inside the fuel tank. The third plot, line 1906, shows generation of an ultrasonic signal from an ultrasonic signal generator (such as ultrasonic signal generator 240 in FIG. 2). The ultrasonic signal generator is coupled to a first wall of the fuel tank, and the generated ultrasonic signal gets reflected from a second, opposite wall of the fuel tank. The reflected ultrasonic signal is recorded by an ultrasonic signal sensor (such as ultrasonic signal sensor 241 in FIG. 2) coupled to the first wall, proximal to the ultrasonic signal generator. The fourth plot, line 1908, shows a fuel age estimation event. Dashed line 1909 shows an estimated fuel age during and after the fuel age estimation event. Dashed line 1910 shows the threshold fuel age above which the operator is notified to change the fuel. The fifth plot, line 1912, shows spark timing relative to maximum brake torque (MBT) timing.

Prior to time t1, the engine is not operated as the vehicle is not propelled via engine torque. Fuel injection and spark is disabled during engine shut-down. At time t1, the engine is started from rest and fuel is injected to engine cylinders via direct injection. Fuel temperature changes are based on engine operation and fuel is not supplied to the fuel tank. Fuel age estimation is not carried out at this time and the ultrasonic signal generator and sensor remain inactive.

At time t2, it is inferred that a threshold duration had elapsed since the previous fuel age determination. Therefore, at time t2, a fuel age estimation is initiated. In order to estimate the fuel age, the ultrasonic signal generator is activated to generate ultrasonic signal. The ultrasonic signal, upon reflection from the opposite wall of the fuel tank is detected by the ultrasonic sensor. A speed of sound in fuel is estimated based on a time of travel of the ultrasonic signal through the fuel, back and forth between a first wall of the fuel tank and a second, opposite, wall of the fuel tank, and a distance between the first wall and the second wall. An attenuation coefficient of the ultrasonic signal is estimated based on a change in amplitude of the ultrasonic signal reaching the ultrasonic signal sensor after being reflected from the second wall. Age of the fuel contained in the fuel tank is estimated based on each of the fuel temperature, the speed of sound in the fuel, and the attenuation coefficient of ultrasonic signal in the fuel. Fuel age estimation is completed at time t3.

After the fuel age estimation, it is confirmed that the fuel age has increased. However, since the fuel age continues to be below the threshold age 1910, the operator is not notified. In response to the increased fuel age, after time t3, the engine is operated with spark timing advanced to MBT. Due to the advanced spark timing, engine efficiency is improved.

In this way, fuel ethanol content or fuel age may be estimated based on reflection of an ultrasonic signal inside a fuel tank and then engine operation such as spark timing may be adjusted to improve fuel efficiency and engine performance.

An example method for an engine comprises: adjusting engine operation based on an estimated fuel age, the fuel age estimated based on at least two of a resonant frequency of pressure pulsations, a change in fuel rail pressure, and a damping coefficient of pressure pulsations in a fuel rail after a fuel injection or pump stroke. In any preceding example, further comprising, additionally or optionally, estimating a fuel ethanol content and/or a fuel water content based on each of the resonant frequency of pressure pulsations, the change in fuel rail pressure, and the damping coefficient of pressure pulsations, and adjusting engine operation based on the estimated fuel ethanol content and/or water content. In any or all of the preceding examples, further comprising, additionally or optionally, estimating a fuel rail temperature as a function of each of the resonant frequency of pressure pulsations, the change in fuel rail pressure, and the damping coefficient of pressure pulsations. In any or all of the preceding examples, additionally or optionally, the fuel ethanol content is a percentage of ethanol in fuel in the fuel tank of an engine of a flexible-fuel vehicle and wherein the fuel water content is a percentage of water in fuel in the fuel rail. In any or all of the preceding examples, additionally or optionally, the fuel age is a function of a duration of storage of fuel in the fuel tank and temperature and pressure of the fuel in the tank, the fuel age indicating a change in fuel constitution due to vaporization of volatile components of the fuel. In any or all of the preceding examples, additionally or optionally, the change in fuel rail pressure is a difference in fuel rail pressure as estimated via a fuel rail pressure sensor coupled to the fuel rail, before and after the fuel injection via an injector coupled to the fuel rail or the pump stroke of a high-pressure fuel pump. In any or all of the preceding examples, additionally or optionally, the resonant frequency of pressure pulsations is estimated based on pressure pulsations as estimated via a fuel rail pressure sensor coupled to the fuel rail immediately after the fuel injection or the pump stroke. In any or all of the preceding examples, additionally or optionally, the damping coefficient is estimated based on one or more of fitting an exponential function to a decaying profile or envelope of the pressure pulsations, Prony analysis, and fast Fourier transform of the decaying profile. In any or all of the preceding examples, additionally or optionally, the fuel ethanol content is estimated periodically at least within a first threshold distance of travel and/or duration of travel after a refueling event and the fuel age is estimated periodically after completion of a second threshold distance of travel and/or duration of travel since an immediately previous fuel age estimation, the second threshold distance of travel and/or duration of travel being higher than the first threshold distance of travel and/or duration of travel. In any or all of the preceding examples, additionally or optionally, adjusting engine operations include adjusting spark timing based on the estimated fuel ethanol content and/or the fuel age, the spark timing advanced to MBT in response to an increase in fuel ethanol content. In any or all of the preceding examples, additionally or optionally, adjusting engine operations further include adjusting an amount of fuel injected during a cold-start based on the estimated fuel ethanol content, fuel water content, and/or fuel age, the amount of fuel injected increased during a cold-start in response to the increase in fuel ethanol and/or water content and an increase in fuel age. In any or all of the preceding examples, the method further comprising, additionally or optionally, adjusting injector pulse width during fuel injection based on the estimated fuel rail temperature. In any or all of the preceding examples, the method further comprising, additionally or optionally, in response to one of an increase in fuel age to above a threshold age and an increase in fuel water content to above a threshold level, notifying an operator to use/change the fuel.

Another example engine method, comprises: during a first condition, estimating volume fractions of ethanol and water in fuel contained in a fuel tank based on each of an estimated fuel bulk modulus, an estimated fuel viscosity, and a speed of sound in fuel, and adjusting engine operation based on the estimated volume fraction of ethanol, during a second condition, estimating an age of the fuel contained in the fuel tank based on at least two the estimated fuel bulk modulus, the estimated fuel viscosity, and the speed of sound in fuel, and adjusting engine operation based on the age of the fuel; and during each of the first condition and the second condition, estimating a fuel rail temperature based on the estimated volume fraction of ethanol in fuel, volume fraction of water in fuel, or age of the fuel, and one of the estimated fuel bulk modulus, the estimated fuel viscosity, and the speed of sound in fuel. In any preceding example, additionally or optionally, the first condition includes completion of a refueling event on a flex-fuel vehicle, and wherein the second condition includes completion of a threshold distance of travel and/or duration of travel since an immediately previous fuel age estimation. In any or all of the preceding examples, additionally or optionally, the fuel bulk modulus is a function of a change in pressure after a fuel pump stroke or injection event, wherein the fuel viscosity is a function of a damping coefficient of pressure pulsations in a fuel rail immediately after the fuel pump stroke or injection event, and wherein the speed of sound in fuel is a function of a resonant frequency of the pressure pulsations in the fuel rail. In any or all of the preceding examples, additionally or optionally, the adjusting engine operation based on the estimated volume fraction of ethanol includes advancing spark timing to MBT in response to an increase in the volume fraction, and wherein the adjusting engine operation based on the age of the fuel includes increasing fuel injection amount during cold-start in response to an increase in fuel age.

Yet another example engine system, comprises: a controller with computer readable instructions stored on non-transitory memory that, when executed, cause the controller to: upon completion of a refueling event, estimate a fuel ethanol content based on fuel rail pressure factors, and adjust one or more of an amount of injected fuel and spark timing based on the estimated fuel ethanol content; and upon completion of a threshold duration since an immediately prior fuel age estimation, estimate fuel age based on fuel rail pressure factors, and adjust one or more of the amount of injected fuel, fuel injection timing, and spark timing based on the estimated fuel age. In any preceding example, additionally or optionally, the fuel rail pressure factors include a change in fuel rail pressure responsive to a stroke of a fuel pump or injection event, a damping coefficient of pressure pulsations in a fuel rail immediately after the stroke or injection event, and a resonant frequency of the pressure pulsations in the fuel rail immediately after the stroke or injection event. In any or all of the preceding examples, additionally or optionally, the fuel pump is fluidically coupled to the fuel rail, and wherein the fuel rail is one a direct injector rail and a port injector rail including a fuel rail pressure sensor.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an engine, comprising:
adjusting engine operation based on an estimated fuel age, the fuel age estimated based on at least two of a resonant frequency of pressure pulsations, a change in fuel rail pressure, and a damping coefficient of pressure pulsations in a fuel rail after a fuel injection or pump stroke.

2. The method of claim 1, further comprising, estimating a fuel ethanol content and/or a fuel water content based on each of the resonant frequency of pressure pulsations, the change in fuel rail pressure, and the damping coefficient of pressure pulsations, and adjusting engine operation based on the estimated fuel ethanol content and/or water content.

3. The method of claim 1, further comprising, estimating a fuel rail temperature as a function of each of the resonant frequency of pressure pulsations, the change in fuel rail pressure, and the damping coefficient of pressure pulsations.

4. The method of claim 1, wherein the fuel ethanol content is a percentage of ethanol in fuel in the fuel tank of an engine of a flexible-fuel vehicle and wherein the fuel water content is a percentage of water in fuel in the fuel rail.

5. The method of claim 1, wherein the fuel age is a function of a duration of storage of fuel in the fuel tank, and temperature and pressure of the fuel in the tank, the fuel age indicating a change in fuel constitution due to vaporization of volatile components of the fuel.

6. The method of claim 4, wherein the change in fuel rail pressure is a difference in fuel rail pressure as estimated via a fuel rail pressure sensor coupled to the fuel rail, before and after the fuel injection via an injector coupled to the fuel rail or the pump stroke of a high-pressure fuel pump.

7. The method of claim 6, wherein the resonant frequency of pressure pulsations is estimated based on pressure pulsations as estimated via a fuel rail pressure sensor coupled to the fuel rail immediately after the fuel injection or the pump stroke.

8. The method of claim 1, wherein the damping coefficient is estimated based on one or more of fitting an exponential function to a decaying profile or envelope of the pressure pulsations, Prony analysis, and fast Fourier transform of the decaying profile.

9. The method of claim 1, wherein the fuel ethanol content is estimated periodically at least within a first threshold distance of travel and/or duration of travel after a refueling event and the fuel age is estimated periodically after completion of a second threshold distance of travel and/or duration of travel since an immediately previous fuel age estimation, the second threshold distance of travel and/or duration of travel being higher than the first threshold distance of travel and/or duration of travel.

10. The method of claim 1, wherein adjusting engine operations include adjusting spark timing based on the estimated fuel ethanol content and/or the fuel age, the spark timing advanced to MBT in response to an increase in fuel ethanol content.

11. The method of claim 9, wherein adjusting engine operations further include adjusting an amount of fuel injected during a cold-start based on the estimated fuel ethanol content, fuel water content, and/or fuel age, the amount of fuel injected increased during a cold-start in response to the increase in fuel ethanol and/or water content and an increase in fuel age.

12. The method of claim 2, further comprising, adjusting injector pulse width during fuel injection based on the estimated fuel rail temperature.

13. The method of claim 1, further comprising, in response to one of an increase in fuel age to above a threshold age and an increase in fuel water content to above a threshold level, notifying an operator to use/change the fuel.

14. An engine method, comprising:
during a first condition,
estimating volume fractions of ethanol and water in fuel contained in a fuel tank based on each of an estimated fuel bulk modulus, an estimated fuel viscosity, and a speed of sound in fuel, and adjusting engine operation based on the estimated volume fraction of ethanol;
during a second condition,
estimating an age of the fuel contained in the fuel tank based on at least two the estimated fuel bulk modulus, the estimated fuel viscosity, and the speed of sound in fuel, and adjusting engine operation based on the age of the fuel; and
during each of the first condition and the second condition,
estimating a fuel rail temperature based on the estimated volume fraction of ethanol in fuel, volume fraction of water in fuel, or age of the fuel, and one of the estimated fuel bulk modulus, the estimated fuel viscosity, and the speed of sound in fuel.

15. The method of claim 13, wherein the first condition includes completion of a refueling event on a flex-fuel vehicle, and wherein the second condition includes completion of a threshold distance of travel and/or duration of travel since an immediately previous fuel age estimation.

16. The method of claim 13, wherein the fuel bulk modulus is a function of a change in pressure after a fuel pump stroke or injection event, wherein the fuel viscosity is a function of a damping coefficient of pressure pulsations in a fuel rail immediately after the fuel pump stroke or injection event, and wherein the speed of sound in fuel is a function of a resonant frequency of the pressure pulsations in the fuel rail.

17. The method of claim 13, wherein the adjusting engine operation based on the estimated volume fraction of ethanol includes advancing spark timing to MBT in response to an increase in the volume fraction, and wherein the adjusting engine operation based on the age of the fuel includes increasing fuel injection amount during cold-start in response to an increase in fuel age.

18. An engine system, comprising:
a controller with computer readable instructions stored on non-transitory memory that, when executed, cause the controller to:
upon completion of a refueling event,
estimate a fuel ethanol content based on fuel rail pressure factors, and adjust one or more of an amount of injected fuel and spark timing based on the estimated fuel ethanol content; and
upon completion of a threshold duration since an immediately prior fuel age estimation,
estimate fuel age based on fuel rail pressure factors, and adjust one or more of the amount of injected fuel, fuel injection timing, and spark timing based on the estimated fuel age.

19. The system of claim 18, wherein the fuel rail pressure factors include a change in fuel rail pressure responsive to a stroke of a fuel pump or injection event, a damping coefficient of pressure pulsations in a fuel rail immediately after the stroke or injection event, and a resonant frequency of the pressure pulsations in the fuel rail immediately after the stroke or injection event.

20. The system of claim 19, wherein the fuel pump is fluidically coupled to the fuel rail, and wherein the fuel rail is one a direct injector rail and a port injector rail including a fuel rail pressure sensor.

* * * * *